United States Patent
Miyoshi et al.

(10) Patent No.: US 9,535,176 B2
(45) Date of Patent: Jan. 3, 2017

(54) RADIATION IMAGE CAPTURING APPARATUS

(71) Applicant: Konica Minolta, Inc., Chiyoda-ku, Tokyo (JP)

(72) Inventors: Kohei Miyoshi, Hachioji (JP); Manabu Kawaguchi, Hachioji (JP); Hiroshi Namekawa, Kawagoe (JP); Takayuki Narita, Tokyo (JP)

(73) Assignee: KONICA MINOLTA, INC, Tokyo (JP)

( * ) Notice: Subject to any disclaimer, the term of this patent is extended or adjusted under 35 U.S.C. 154(b) by 0 days.

(21) Appl. No.: 14/681,572

(22) Filed: Apr. 8, 2015

(65) Prior Publication Data
US 2015/0293239 A1 Oct. 15, 2015

(30) Foreign Application Priority Data

Apr. 9, 2014 (JP) ................................. 2014-079978
Dec. 10, 2014 (JP) ................................. 2014-249514

(51) Int. Cl.
*G01T 7/00* (2006.01)
*A61B 6/00* (2006.01)
*G03B 42/04* (2006.01)

(52) U.S. Cl.
CPC ............... *G01T 7/00* (2013.01); *A61B 6/4283* (2013.01); *G03B 42/04* (2013.01)

(58) Field of Classification Search
CPC ......... G01T 17/00; G01T 1/70; A61B 6/4283; G03B 42/04
USPC ........................................................ 378/182
See application file for complete search history.

(56) References Cited

U.S. PATENT DOCUMENTS

| | | | | |
|---|---|---|---|---|
| 2007/0109730 | A1* | 5/2007 | Shigyo ................ | H05K 5/0052 361/600 |
| 2010/0038549 | A1* | 2/2010 | Nishino ................ | G03B 42/04 250/370.09 |
| 2011/0069814 | A1* | 3/2011 | Yonekawa ............... | A61B 6/00 378/62 |
| 2013/0082184 | A1* | 4/2013 | Nakatsugawa ...... | A61B 6/4208 250/366 |

FOREIGN PATENT DOCUMENTS

JP 2012181044 A 9/2012

* cited by examiner

*Primary Examiner* — Yara B Green
(74) *Attorney, Agent, or Firm* — Cantor Colburn LLP

(57) ABSTRACT

Disclosed is a radiation image capturing apparatus including the following. A sensor panel includes a plurality of radiation detecting elements aligned two-dimensionally. A case stores the sensor panel. A ventilation hole is provided in the case. A ventilation filter is provided in the ventilation hole and prevents infiltration of liquid into the case. Air flows in and out of the case through the ventilation hole and a thickness of the case is maintained at a predetermined thickness when outside pressure changes.

11 Claims, 13 Drawing Sheets

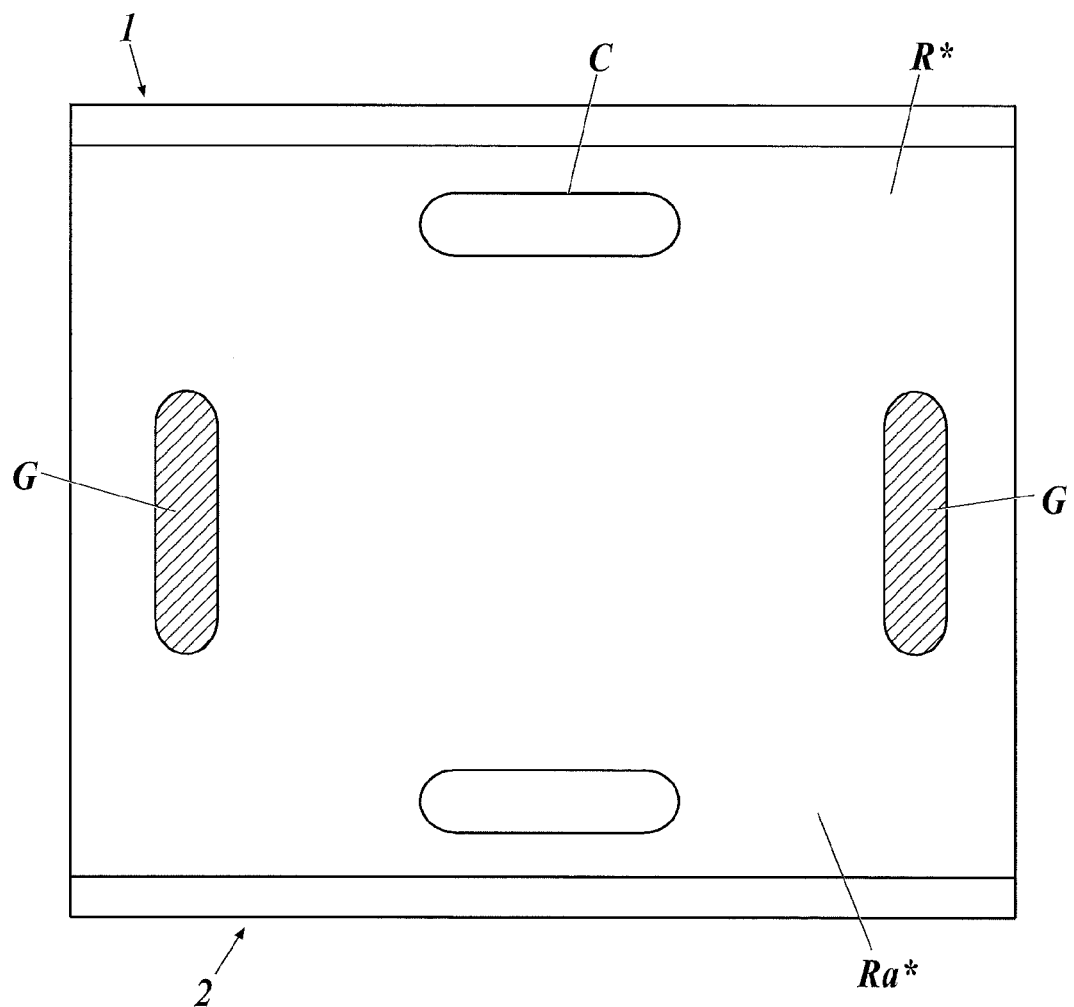

RADIATION IMAGE CAPTURING APPARATUS

CROSS REFERENCE TO RELATED APPLICATIONS

The present invention claims priority under 35 U.S.C. §119 to Japanese Application No. 2014-079978 filed Apr. 9, 2014 and Japanese Application No. 2014-249514 filed Dec. 10, 2014, the entire contents of which are incorporated herein by reference.

BACKGROUND

Field of the Invention

The present invention relates to a radiation image capturing apparatus. Specifically, the present invention relates to a radiation image capturing apparatus in which radiation detecting elements are aligned two dimensionally.

Description of Related Art

Various radiation image capturing apparatuses are developed. In such radiation image capturing apparatuses, charge is generated in a detecting element according to dose of radiation of irradiated X-ray, etc. and the generated charge is read out as image data. Such type of radiation image capturing apparatus is known as an FPD (Flat Panel Detector), and conventionally such apparatus was configured as a dedicated apparatus type (fixed type) formed as one with a supporting base, etc. Lately, a portable type (cassette type) radiation image capturing apparatus where the detecting element, etc. is stored in a case so that it can be carried is developed and being implemented.

Similar to a CR (Computed Radiography) cassette used in conventional radiation image capturing, such portable radiation image capturing apparatuses can be used for capturing in a state loaded on a bucky apparatus (see later described FIG. 4), held directly against a patient's body, or with the patient laid on the apparatus. The above features are features which dedicated apparatus type radiation image capturing apparatuses do not have.

However, when the radiation image capturing apparatus is used as described above in a state held directly against the patient's body or with the patient laid on the radiation image capturing apparatus, urine, blood, etc. of the patient may be attached to the radiation image capturing apparatus. When the urine, blood, etc. attached to the radiation image capturing apparatus infiltrates into the case of the apparatus, problems may occur such as a short circuit may occur or components may be damaged or broken in a sensor panel provided with electronic components, etc. (see later described SP of FIG. 2) in the case due to the infiltrated urine.

Therefore, Japanese Patent Application Laid-Open Publication No. 2012-181044 discloses a radiation image capturing apparatus configured to be provided with a waterproof member in a portion where a lid is fitted to a main body portion of a case so that the case includes a waterproof function.

When the waterproof performance of the radiation image capturing apparatus is enhanced by providing packing or a rubber or resin sealing member in a portion where a gap is formed in the case, hermetic performance of the case is also enhanced. However, when the highly airtight radiation image capturing apparatus is in an environment where outside pressure is low such as when used in facilities such as hospitals in highlands or when transported flying highly above in the air by aircraft, there is a difference between the pressure in the case (1 atmospheric pressure) and outside pressure (less than 1 atmospheric pressure).

When the case is strong enough to stand the pressure difference, expansion of the case can be suppressed. However, radiation image capturing apparatuses are usually thin, and the weight cannot be made heavy limitlessly. Therefore, in practice, it is difficult to make the case strong enough to stand the pressure difference. Therefore, the case of the radiation image capturing apparatus expands.

When the case of the radiation image capturing apparatus expands, the following problems may occur, such as, the packing, sealing, etc. provided to prevent the patient's urine, blood, etc. from infiltrating into the case of the radiation image capturing apparatus is removed or damaged, and the patient's urine, etc. is able to infiltrate into the case or the member in the apparatus is damaged or does not function properly due to the expansion of the case.

When the case of the radiation image capturing apparatus expands, the radiation image capturing apparatus cannot be loaded on the bucky apparatus, and capturing in a state loaded on the bucky apparatus may not be performed properly. Further, when the case of the radiation image capturing apparatus is used in an expanded state, the distance between the radiation detecting elements provided on the sensor panel in the case and the body of the patient which is the subject becomes far in the center portion of the radiation entering face (see later described R shown in FIG. 1 and FIG. 2) of the case expanded and rising and close in the periphery portion of the radiation entering face. Therefore, the image of the captured subject becomes an image with a blurred center portion, and the image cannot be suitably captured.

SUMMARY

The present invention has been made in consideration of the above problems, and one of the main objects is to provide a radiation image capturing apparatus in which expansion of a case can be reliably prevented even when the outside pressure decreases.

In order to achieve at least one of the above-described objects, according to an aspect of the present invention, there is provided a radiation image capturing apparatus including:

a sensor panel which includes a plurality of radiation detecting elements aligned two-dimensionally;

a case which stores the sensor panel;

a ventilation hole which is provided in the case; and a ventilation filter which is provided in the ventilation hole and which prevents infiltration of liquid into the case, wherein air flows in and out of the case through the ventilation hole and a thickness of the case is maintained at a predetermined thickness when outside pressure changes.

According to the radiation image capturing apparatus of the present invention, a ventilation hole is provided. Therefore, the air inside and outside the case of the radiation image capturing apparatus can pass through the ventilation hole. When the outside pressure becomes low, the air flows out from inside the case through the ventilation hole, and when the outside pressure becomes high, the air flows into the case through the ventilation hole. With this, even if the outside pressure changes, the pressure inside the case is also changed and the pressure inside and outside the case can be made the same. Consequently, even if the outside pressure decreases, it is possible to reliably prevent the case from expanding, and the thickness of the case can be maintained to a predetermined thickness.

BRIEF DESCRIPTION OF THE DRAWINGS

The present invention will become more fully understood from the detailed description given hereinbelow and the appended drawings, and thus are not intended to define the limits of the present invention, and wherein;

FIG. 8 is a diagram showing a cutout and grip member provided in a face plate attached to a rear face of a case of the radiation image capturing apparatus;

DETAILED DESCRIPTION OF PREFERRED EMBODIMENTS

The embodiment of the radiation image capturing apparatus of the present invention is described with reference to the drawings.

Described below is an indirect type radiation image capturing apparatus which includes a scintillator, etc. and which converts radiated radiation to an electromagnetic wave with another wavelength such as visible light to obtain image data with the radiation detecting element. However, the present invention can also be applied to a direct type radiation image capturing apparatus which directly detects the radiation with the radiation detecting element without using the scintillator, etc.

[Basic Configuration of Radiation Image Capturing Apparatus]

Figure 1:
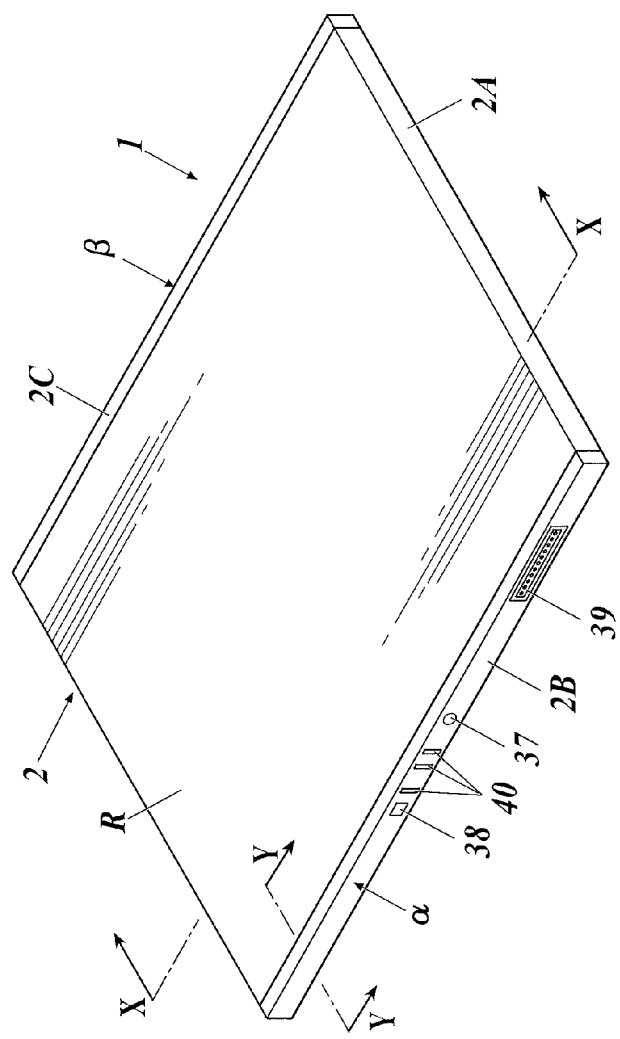
FIG. 1 is a perspective view showing an external appearance of a radiation image capturing apparatus of the present embodiment.
Figure 2:
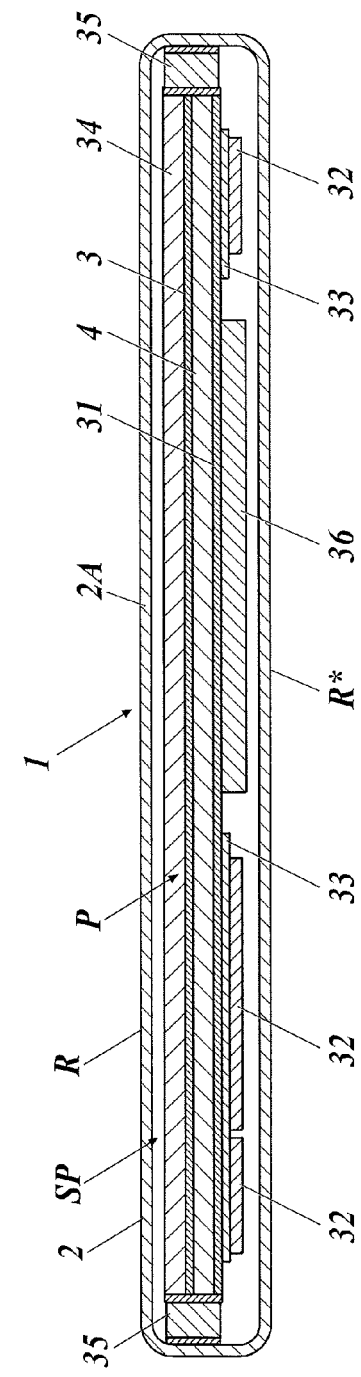
FIG. 2 is a cross-sectional view along line X-X shown in FIG. 1.

The basic configuration, etc. of the radiation image capturing apparatus of the present embodiment is briefly described. FIG. 1 is a perspective view showing an external appearance of the radiation image capturing apparatus. FIG. 2 is a cross-sectional view along line X-X shown in FIG. 1. In order to simplify the description, the vertical direction shown in FIG. 2 is to be the vertical direction of the radiation image capturing apparatus 1.

As shown in FIG. 1, the radiation image capturing apparatus 1 includes a case 2 with a radiation entering face R which is the face on the side where the radiation is irradiated. A sensor panel SP including a scintillator 3, sensor substrate 4, etc. is stored in the case 2. Therefore, the radiation image capturing apparatus 1 is portable. In FIG. 2, R* shows the face of the case 2 on the opposite side of the radiation entering face R. Down below, the face R* is referred to as rear face R*.

As shown in FIG. 1 and FIG. 2, according to the present embodiment, the case 2 is formed as follows. A housing main body portion 2A in a hollow square tube shape including the radiation entering face R is formed with a carbon plate (in other words, carbon fiber fixed in a plate shape with resin, etc.) which passes radiation. The openings on both sides of the housing main body portion 2A are blocked with protecting covers 2B and 2C.

Alternatively, instead of blocking the openings on both sides of the square tube shaped housing main body unit 2A with protecting covers 2B and 2C to form the case 2 of the radiation image capturing apparatus 1, although illustration is omitted, for example, a lunch box type case is possible. For example, such case can be as follows, when the sensor panel SP is positioned so that the face is in a horizontal direction as shown in FIG. 2, the sensor panel SP is stored so that the sensor panel SP is covered from above and below.

According to the present embodiment, an antenna 41 (illustration is omitted in FIG. 1 and FIG. 2, see later described FIG. 4) to communicate wirelessly with external apparatuses is included inside portions α and β of the protecting covers 2B and 2C. The protecting cover 2B on one side of the case 2 is provided with a power source switch 37, a switching switch 38, a connector 39, and an indicator 40 including an LED (Light Emitting Diode) displaying the state of the battery and operation of the apparatus.

As shown in FIG. 2, a base 31 is positioned in the case 2. A sensor substrate 4 is provided on the upper side of the base 31 (in other words, the radiation entering face R side) with a lead thin plate (not shown) in between. A scintillator 3 which converts the irradiated radiation to light such as visible light, etc., and a scintillator substrate 34 which supports the scintillator 3 is provided on the upper face side of the sensor substrate 4.

Figure 3:
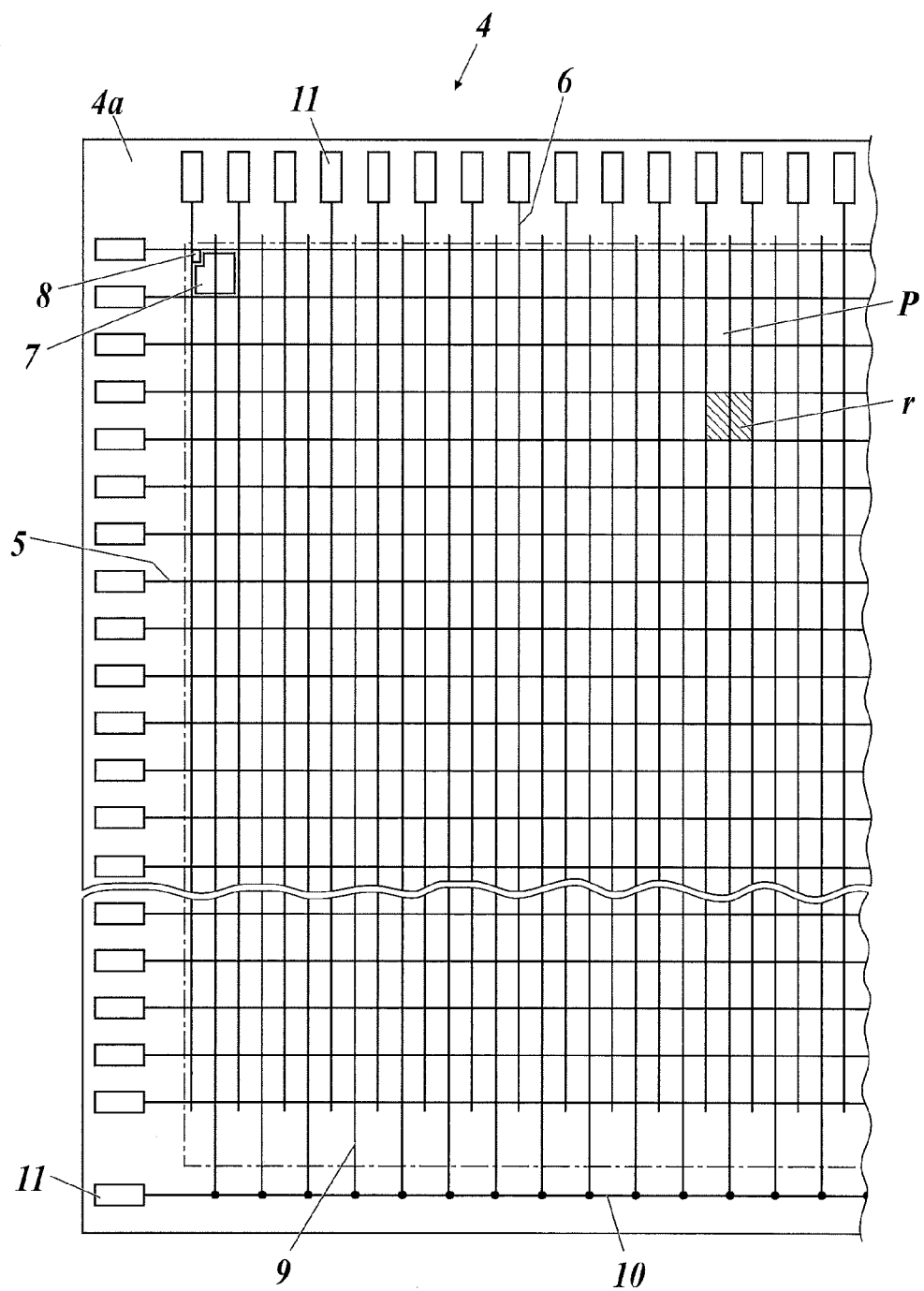
FIG. 3 is a planar view showing a configuration of a substrate of a radiation image capturing apparatus.

According to the present embodiment, as shown in FIG. 3, the sensor substrate 4 is composed from a glass substrate, and a plurality of scanning lines 5 and a plurality of signal lines 6 are provided on an upper face 4a (in other words, the face facing the scintillator 3) of the sensor substrate 4 so as to intersect with each other. Each small region r divided by the plurality of scanning lines 5 and the plurality of signal lines 6 on the face 4a of the sensor substrate 4 is provided with a radiation detecting element 7.

The entire region of the small regions r, each small region r divided by the scanning line 5 and the signal line 6 and provided with a plurality of radiation detecting elements 7 arranged two-dimensionally (matrix shape) is considered to be a detecting section P. The detecting section P is the region shown with alternate long and short dash lines in FIG. 3. According to the present embodiment, photodiode is used as the radiation detecting element 7. Alternatively, for example, a phototransistor, etc. can be used.

A PCB substrate 33 provided with an electronic component 32, etc. and a battery 36 are attached to the lower face side of the substrate 31. The scanning lines 5 and the signal lines 6 provided on the face 4a of the sensor substrate 4 are guided to the lower face side of the base 31 through an input/output terminal 11 (see FIG. 3) and a flexible circuit substrate (not shown, also called Chip On Film, etc.), and the lines are connected to various electronic components 32.

As shown in FIG. 3, a bias line 9 is connected to each radiation detecting element 7, and each bias line 9 is connected to line 10 at the periphery portion of the upper face 4a of the sensor substrate 4. The line 10 is connected to a bias supply (not shown) on the lower face side of the base 31 through the input/output terminal 11 and the flexible circuit substrate. Reverse bias voltage supplied from the bias supply is applied to each radiation detecting element 7 through the line 10 and the bias line 9.

According to the present embodiment, the sensor panel SP (see FIG. 2) of the radiation image capturing apparatus 1 is formed as described above. Moreover, according to the present embodiment, cushioning material 35 is provided between the sensor panel SP and inner side of the case 2.

Figure 4:
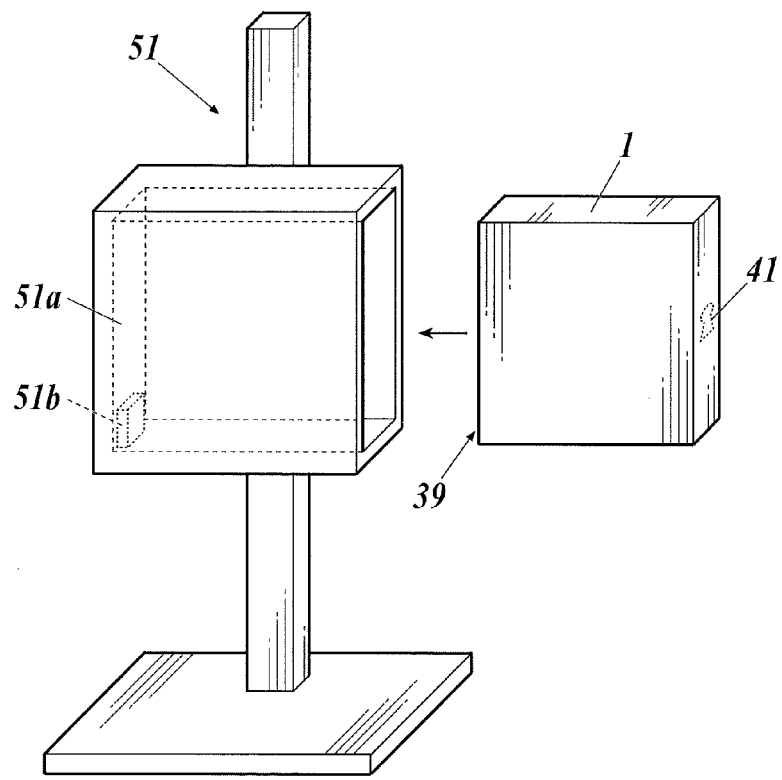
FIG. 4 is a diagram describing a bucky apparatus.

Similar to the above described conventional radiation image capturing apparatus, the radiation image capturing apparatus 1 of the present embodiment can be used in a state held directly against the body of the patient or in a state where the patient lies on the case 2. Moreover, as shown in FIG. 4, the radiation image capturing apparatus 1 is formed in a size so that the apparatus can be loaded on the cassette holding unit (also called cassette holder, etc.) 51a of the bucky apparatus 51, and the radiation image capturing apparatus 1 can be used loaded on the bucky apparatus 51. FIG. 4 shows a configuration in which the connector 39 of the radiation image capturing apparatus 1 is automatically connected to the connector 51b of the bucky apparatus 51 provided in the cassette holding unit 51a when the radiation image capturing apparatus 1 is loaded on the cassette holding unit 51a of the bucky apparatus 51.

According to the present embodiment, the case 2 of the radiation image capturing apparatus 1 is formed so that the radiation image capturing apparatus 1 can be loaded on the bucky apparatus 51 similar to the CR cassette widely used in facilities such as hospitals. Normally, the CR cassette is formed in a size conforming to JIS standard size (JIS Z4905 (corresponding international standard is IEC 60406)) for conventional screen/film cassettes. Therefore, the radiation image capturing apparatus 1 of the present embodiment is formed in a size conforming to the JIS standard size. In other words, at least the thickness of the case 2 in the radiation entering direction (in other words, the space between the radiation entering face R and the rear face R* of the case 2) is formed within a range of 13 to 16 [mm].

[Configuration to Prevent Expansion of Case]

Described next is the configuration of the radiation image capturing apparatus 1 of the present embodiment to reliably prevent the case 2 from expanding due to decrease in outside pressure, etc. as described above.

Regarding the above, according to the present embodiment, the case 2 of the radiation image capturing apparatus 1 is provided with a ventilation hole. The ventilation hole is provided with a ventilation filter to prevent liquid such as urine of the patient from infiltrating into the case 2. Air is able to flow in and out of the case 2 through the ventilation hole. Therefore, even if the outside pressure changes such as reduction of the pressure, at least the thickness (in other words, space between the radiation entering face R and the rear face R* in FIG. 2) of the case 2 is maintained to a predetermined thickness.

In other words, according to the present embodiment, as described above, the thickness of the case 2 of the radiation image capturing apparatus 1 is 13 to 16 [mm] which is the size conforming to the JIS standard size. Therefore, the ventilation hole is formed so that at least the thickness of the case 2 is maintained within the above range.

The above described ventilation hole can be provided in a portion of the rear face R* of the housing main body unit 2A (see FIG. 2, etc.) of the case 2, or a portion of the radiation entering face R, specifically, the periphery portion of the radiation entering face R which is not above the above described detecting unit P (see FIG. 3), or the side face of the housing main body unit 2A. According to the present embodiment, the ventilation hole is provided on the side face portion of the case 2 where the protecting covers 2B and 2C are attached.

Figure 5:
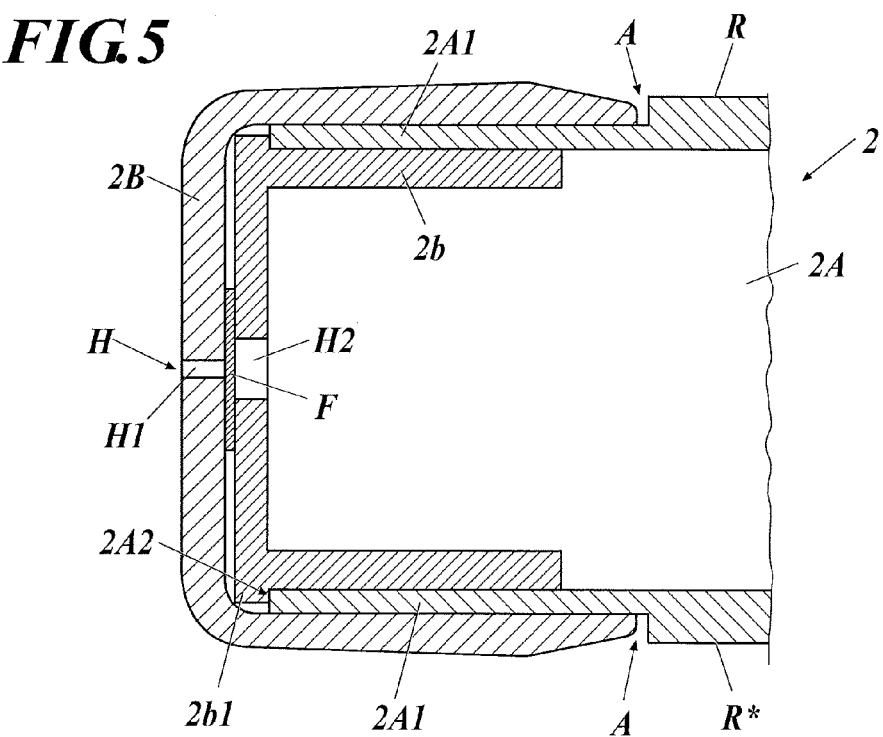
FIG. 5 is a cross-sectional view along line Y-Y shown in FIG. 1.

The structure is described in detail below. According to the present embodiment, the structure of the side face portion of the case 2 where the protecting covers 2B and 2C are attached is a structure as shown in FIG. 5, for example. FIG. 5 is a cross-sectional view along line Y-Y shown in FIG. 1. Reference sign A shown in FIG. 5 is described later. In the example described below, the ventilation hole is provided in the protecting cover 2B. Alternatively, the ventilation hole can be provided in the protecting cover 2C or in both protecting covers 2B and 2C.

According to the present embodiment, as shown in FIG. 5, an inside cover 2b can be attached to an edge portion 2A1 of the housing main body unit 2A of the case 2. The inside cover 2b is inserted on the inside of the edge portion 2A1. A latching portion 2b1 provided in the inside cover 2b latches to a tip 2A2 of the edge portion 2A1 of the housing main body unit 2A so that an opening of the housing main body unit 2A is sealed with the inside cover 2b. The protecting cover 2B is attached to the edge portion 2A1 of the housing main body unit 2A where the inside cover 2b is inserted so as to cover the above from the outside. With this, the opening of the housing main body unit 2A is blocked.

According to the present embodiment, the edge portion 2A1 where the protecting cover 2B is attached in the housing main body unit 2A of the case 2 is very thin. When the protecting cover 2B is attached to this portion, the outer face of the protecting cover 2B and the outer face of the housing main body unit 2A (in other words, the radiation entering face R and the rear face R*) are substantially the same plane. According to such configuration, for example, when the radiation image capturing apparatus 1 is inserted between a bed and a patient lying on the bed, it is possible to prevent the protecting cover 2B from being caught by clothes of the patient.

The protecting cover 2B can be formed from, for example, resin, etc. The inside cover 2b can be formed from metal such as magnesium (Mg), aluminum (Al), or the like. Alternatively, the above can be made from other material as described later.

According to the present embodiment, with such configuration, as shown in FIG. 5, holes H1 and H2 are punched in the protecting cover 2B and the inside cover 2b respectively, and the above holes are provided in a position so as to connect to each other. With this, the ventilation hole H is formed on the side face of the case 2 of the radiation image capturing apparatus 1. By simply providing the ventilation hole H, liquid such as the patient's urine may infiltrate into the case 2 through the ventilation hole H. Therefore, in order to prevent infiltration of the liquid into the case 2 and to enable ventilation, the ventilation filter F is provided in the ventilation hole H.

According to the above configuration, the air flows in and out of the case 2 from the ventilation hole H formed with holes H1 and H2 provided respectively in the protecting cover 2B and the inside cover 2b through the ventilation filter F.

A film consisting of fluorine based resin such as PTFE (polytetrafluoroethylene) porous film can be used as the ventilation filter F in order to prevent the flow of liquid and to enable flow of air in and out of the case 2. Alternatively, a film with ventilation qualities composed of material other than the above can be used as long as the material includes the above functions.

FIG. 5 describes a configuration in which the ventilation filter F is simply placed between the protecting cover 2B and the inside cover 2b. However, although illustration is omitted, for example, the ventilation filter F can be attached to the protecting cover 2B and the inside cover 2b with sealing tape, etc. to prevent the liquid from infiltrating into the case 2 by flowing between the ventilation filter F and the protecting cover 2B or the ventilation filter F and the inside cover 2b.

In FIG. 5, the actual size of the ventilation hole H, etc. in the radiation image capturing apparatus 1 and the actual thickness of each member such as the protecting cover 2B is not always reflected accurately. If the size of the ventilation hole H is made too large, the liquid easily flows into the case 2 through the ventilation hole H, the strength of the portion where the ventilation hole H is formed in the inside cover 2b, etc. becomes weak, fingers and protruding objects touch the ventilation filter from outside and damage the ventilation filter or the ventilation filter may become dirty with stain from outside. Therefore, the size of the ventilation hole H is made in a suitable size so as not to receive bad influence as described above.

The shape of the ventilation hole H is a circular shape according to the present embodiment. Alternatively, the shape of the ventilation hole H can be formed in a different shape and the ventilation hole H is formed with a suitable shape. Due to the above reasons, preferably, the size of the ventilation hole H is made with the narrowest portion of the width of the shape being about 0.5 to 5 [mm]. When the shape is a circle, preferably, the diameter is about 0.5 to 5 [mm].

Figure 6A:
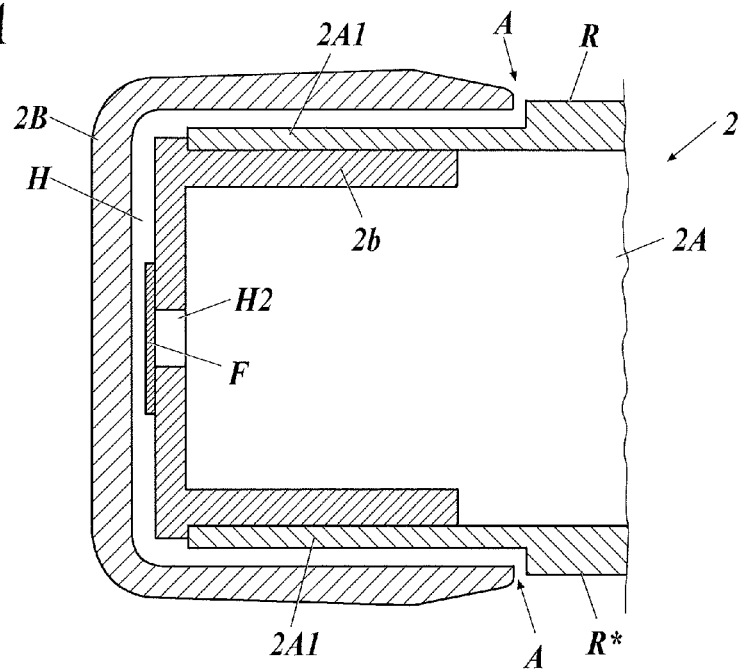
FIG. 6A is a cross-sectional view showing a modification of a configuration shown in FIG. 5.

Further, FIG. 5 describes a configuration in which the ventilation filter F is simply placed between the protecting cover 2B and the inside cover 2b. Alternatively, as shown in FIG. 6A, the hole H1 (see FIG. 5) is not provided in the protecting cover 2B, the hole H2 is provided only in the inside cover 2b, and the ventilation filter F is provided in the portion where the hole H2 is provided in the inside cover 2b. A gap so that air can pass sufficiently and which is connected to the outside can be provided between the protecting cover 2B, and the inside cover 2b and the edge portion 2A1 of the housing main body unit 2A of the case 2. With this, the air can pass through the gap.

In other words, in this case, the ventilation hole H is formed with the hole H2 provided in the inside cover 2b and the gap between the protecting cover 2B, and the inside cover 2b and the edge portion 2A1 of the housing main body unit 2A. The air passes the hole H2 provided in the inside cover 2b and the gap between the protecting cover 2B, and the inside cover 2b and the edge portion 2A1 of the housing main body unit 2A of the case 2, and the air flows in and out through the A portion (see FIG. 6A). According to such configuration, it is possible to prevent the ventilation filter from being damaged by the finger or protruding object directly touching the ventilation filter or from becoming dirty with stain from outside.

When a gap is formed between the protecting cover 2B and the edge portion 2A1 of the housing main body unit 2A of the case 2, the gap can be formed only in the portion where the hole H2 is formed in the inside cover 2b, and the portion of the protecting cover 2B other than the gap can be in close contact with the edge portion 2A1 of the housing main body unit 2A so that the protecting cover 2B is fixed to the edge portion 2A1 of the housing main body unit 2A. In other words, although illustration is omitted, for example, a groove can be provided on the inner face of the protecting cover 2B facing the edge portion 2A1 of the housing main body unit 2A and the portion other than the groove on the inner side of the protecting cover 2B can come into close contact with the edge portion 2A1 of the housing main body unit 2A so that the portion of the groove can be the above described gap.

The entire protecting cover 2B can be in a state raised from the edge portion 2A1 of the housing main body unit 2A of the case 2 (in other words, separated from the edge potion 2A1), a convex portion which projects inside can be provided in a predetermined position on the inner face of the protecting cover 2B, and the convex portion can come into contact with (or be pressed to) the edge portion 2A1 of the housing main body unit 2A to fix the protecting cover 2B to the edge portion 2A1 of the housing main body unit 2A.

Alternatively, although illustration is omitted, the entire protecting cover 2B can be in a state raised from the edge portion 2A1 of the housing main body unit 2A of the case 2, and packing can be positioned scattered throughout the inner face of the protecting cover 2B instead of the convex portion. Also, packing can be provided to form the above described groove on the inner face of the protecting cover 2B and the above packing is placed in close contact with both the protecting cover 2B and the edge portion 2A1 of the housing main body unit 2A so that the gap is formed between the protecting cover 2B and the edge portion 2A1 of the housing main body unit 2A while the protecting cover 2B is fixed to the edge portion 2A1 of the housing main body unit 2A.

In order to test the product with the waterproof function (in other words, the radiation image capturing apparatus 1) prior to shipment and to guarantee the sealing performance, usually, a test called an air leakage test is performed. The air leakage test is broadly categorized into an internal pressure method and an external pressure method. With the internal pressure method, the leakage of the air from the product is detected by the change inside the product before and after a certain amount of time after the pressure inside the product is increased or decreased, and the sealing performance is tested. With the external pressure method, the product is placed in a sealed container, and the leakage of the air from the product is detected by the change inside the sealed container before and after a certain amount of time after the pressure inside the sealed container is increased or decreased, and the sealing performance is tested. In both methods, the sealing performance of the product is tested by the air flowing in and flowing out. Therefore, when the ventilation filter F is provided, the air flows in and out from the ventilation filter F and the sealing performance of the waterproof structure of the other portions cannot be correctly tested.

Therefore, when the product provided with the ventilation filter F is tested with the air leakage test, the test needs to be performed with the ventilation filter F blocked. For example, with the structure as described in FIG. 5, the ventilation hole H can be relatively easily blocked from outside with tape or a tool with packing, both of which are not shown.

Figure 6B:
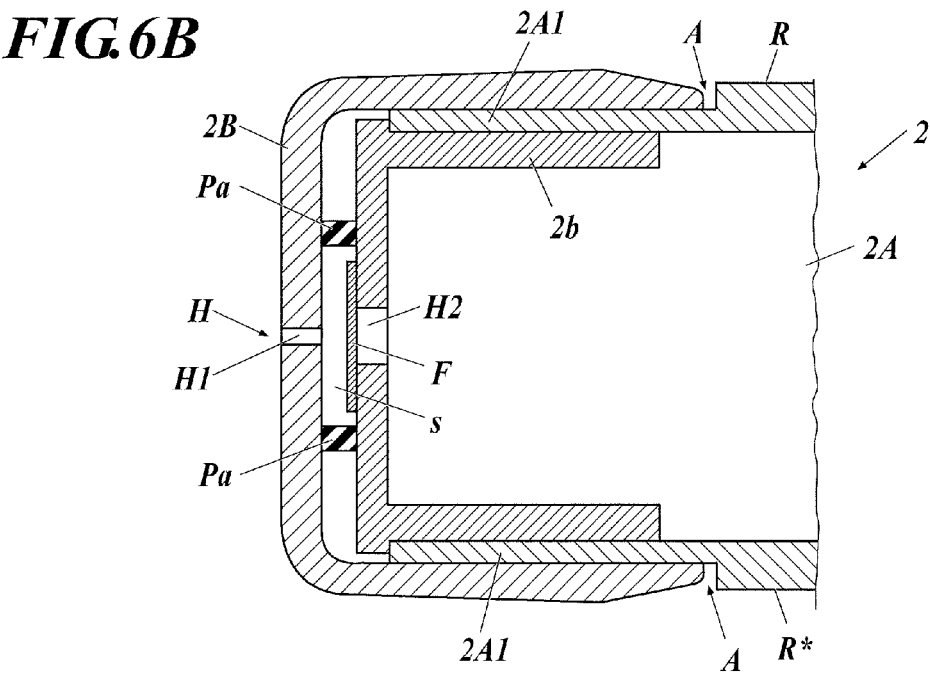
FIG. 6B is a cross-sectional view showing a modification of a configuration shown in FIG. 5.

As shown in FIG. 6B, the holes H1 and H2 are provided in the protecting cover 2B and the inside cover 2b respectively, the ventilation filter F is provided so as to cover the hole H2 of the inside cover 2b, and the holes H1 and H2 form the ventilation hole H. Here, as shown in FIG. 6B, packing Pa can be placed in the portion surrounding the hole H2 (here, surrounding the ventilation filter F) between the inside cover 2b and the protecting cover 2B, and a space s divided by the inside cover 2b, the protecting cover 2B and the packing Pa can be formed.

According to such configuration, the outside air flowing into the inside of the case 2 and the air inside the case 2 flowing outside passes through the holes H1 and H2 provided respectively in the protecting cover 2B and the inside cover 2b, and the space s divided by the inside cover 2b, the protecting cover 2B and the packing Pa, and passes through the ventilation filter F. Therefore, in this case, the ventilation hole H is formed with the holes H1 and H2 provided respectively in the protecting cover 2B and the inside cover 2b, and the space s divided by the inside cover 2b, the protecting cover 2B and the packing Pa.

As described above, the ventilation hole H can be blocked relatively easily from outside with tape or tools with packing (not shown), and by performing the air leakage test in such state, the sealing performance of the waterproof structure in the portion other than the ventilation hole H can be correctly tested.

Figure 7A:
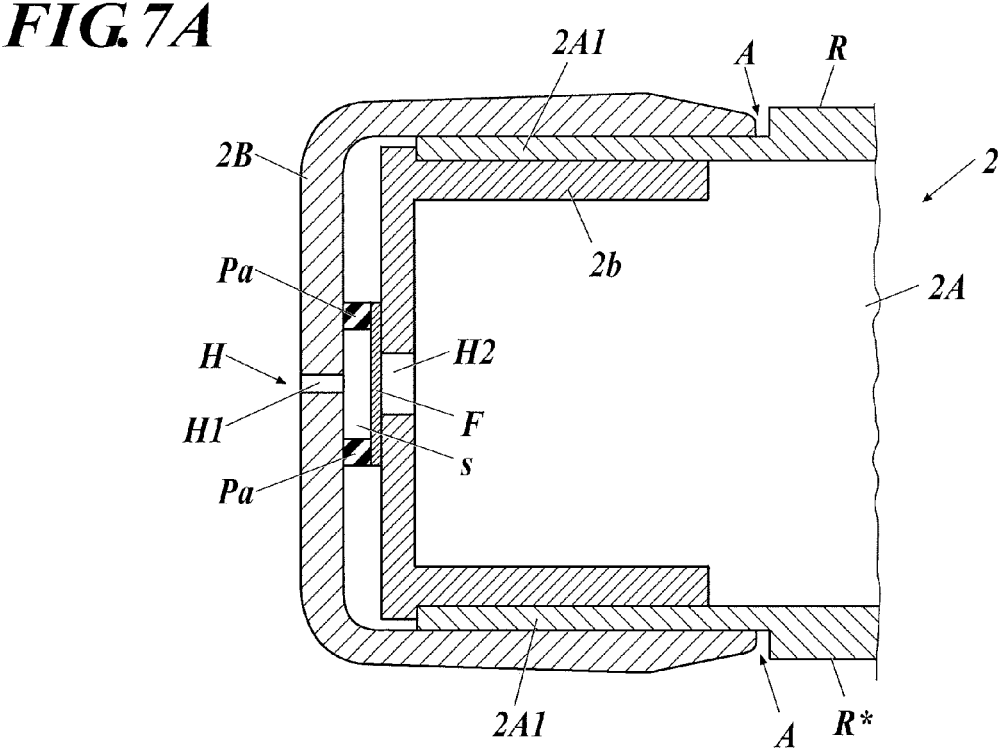
FIG. 7A is a cross-sectional view showing a modification of a configuration shown in FIG. 5.
Figure 7B:
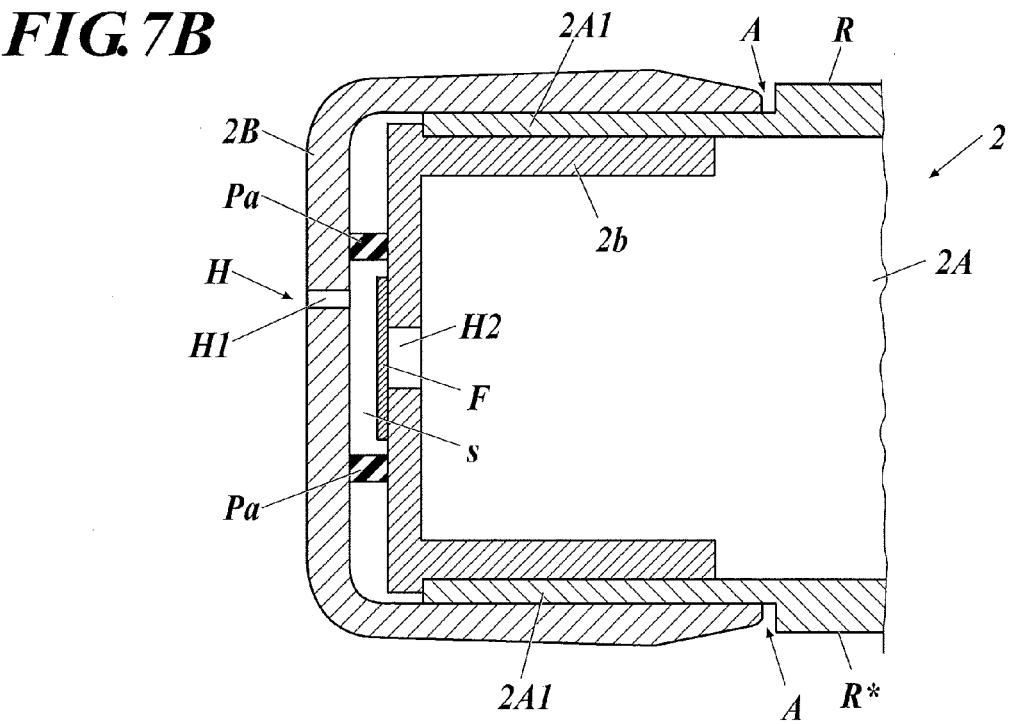
FIG. 7B is a cross-sectional view showing a modification of a configuration shown in FIG. 5.

FIG. 6B, and the later described FIG. 7A and FIG. 7B describe a configuration in which the protecting cover 2B is in close contact with the edge portion 2A1 of the housing main body unit 2A of the case 2. Alternatively, as shown in FIG. 6A, a gap can be provided between the above. FIG. 6B describes an example in which the packing Pa is provided in a portion surrounding the hole H2, specifically, the portion surrounding the ventilation filter F. Other than the above, as shown in FIG. 7A, the packing Pa can be provided on the ventilation filter F surrounding the hole H2. In other words, the packing Pa and the ventilation filter F can be placed between the protecting cover 2B and the inside cover 2b.

FIG. 6B and FIG. 7A describe forming the hole H1 of the protecting cover 2B on the extending line of the hole H2 of the inside cover 2b. Alternatively, as shown in FIG. 7B, the holes H1 and H2 can be formed so that the center axis of the hole H1 of the protecting cover 2B and the center axis of the hole H2 of the inside cover 2b are misaligned. According to such configuration, even if fingers or projecting objects touch the ventilation filter F from outside through the hole H1 of the protecting cover 2B, since the ventilation filter F is fixed to the inside cover 2b at this portion (in other words, it is not the portion where the hole H2 is), the risk of damaging the ventilation filter F can be decreased.

[Function]

The function of the radiation image capturing apparatus 1 of the present embodiment is described. According to the present embodiment, the configuration of the radiation image capturing apparatus 1 is as described above. Therefore, for example, when the radiation image capturing apparatus is carried to an environment in which the outside pressure is low, such as being conveyed from a location with a low altitude to a location with a high altitude, or the apparatus such as being transported by flying in an airplane, the pressure inside the case 2 of the radiation image capturing apparatus 1 becomes higher than the outside pressure.

However, when the pressure in the case 2 becomes higher than the outside pressure, the air inside the case 2 passes the ventilation hole H and flows outside the case 2. With this, the pressure in the case 2 of the radiation image capturing apparatus 1 becomes the same pressure as the outside pressure. Therefore, even if the outside pressure decreases, the case 2 does not expand, and the thickness of the case 2 is maintained at a predetermined thickness (for example, the above described JIS standard size 13 to 16 [mm]).

For example, when the radiation image capturing apparatus 1 is carried from an environment in which the outside pressure is low as described above to a location in which the outside pressure is high, such as a location with low altitude, the pressure in the case 2 of the radiation image capturing apparatus 1 becomes lower than the outside pressure. In this case, the outside air passes through the ventilation hole H of the case 2 and flows into the case 2. Then, the pressure in the case 2 of the radiation image capturing apparatus 1 becomes the same as the outside pressure. Therefore, even if the outside pressure increases, the case 2 is not pressed and dented by the outside pressure, and the thickness of the case 2 is maintained at a predetermined thickness.

Since the ventilation filter F is provided in the ventilation hole H, even if the ventilation hole H is provided in the case 2 of the radiation image capturing apparatus 1, it is possible to reliably prevent the liquid such as the patient's urine from flowing through the ventilation hole H and infiltrating into the case 2 by the ventilation filter F.

[Effect]

As described above, according to the radiation image capturing apparatus 1 of the present embodiment, the ventilation hole H is provided in the case 2, and the ventilation filter F to prevent the infiltration of the liquid into the case 2 is provided in the ventilation hole H. In order to enable the flow of air in and out of the case 2, when the outside pressure becomes low, the air inside the case 2 flows out through the ventilation hole H. When the outside pressure becomes high, the air in the case 2 flows in through the ventilation hole H.

Therefore, even if the outside pressure changes, the pressure in the case 2 can be changed accordingly so that the pressure inside and outside the case 2 is the same. Therefore, according to the radiation image capturing apparatus 1 of the present embodiment, the expansion of the case 2 can be reliably prevented even if the outside pressure decreases, and at least the thickness of the case 2 can be maintained at a predetermined thickness.

Then, since the expansion of the case 2 can be reliably prevented, it is possible to reliably prevent the packing, sealing etc. from peeling or being damaged by the expansion of the case 2, and the liquid such as the patient's urine from infiltrating into the case 2 of the radiation image capturing apparatus 1. Moreover, it is possible to reliably prevent the member in the apparatus from being damaged and not functioning properly or the image not being able to be suitably captured using the radiation image capturing apparatus 1 due to the expansion of the case 2.

[Configuration to Enhance Gripping Performance of Radiation Image Capturing Apparatus]

As described above, the radiation image capturing apparatus 1 of the present embodiment is portable and can be carried (see FIG. 1, FIG. 2, etc.). The radiation image capturing apparatus 1 can also be used in a state alone without loading on the bucky apparatus 51 (see FIG. 4), and the radiation image capturing apparatus 1 can be placed against the body of the patient or inserted between the bed and the patient lying on the bed.

According to the present embodiment, a face plate describing the product name and specifications of the radiation image capturing apparatus 1 is attached to the rear face R* (see FIG. 2, etc.) side of the case 2 of the radiation image capturing apparatus 1. In order to prevent the corner or the edge of the face plate from being caught by the bed or the patient's clothes while the radiation image capturing apparatus 1 is inserted between the patient and the bed, instead of attaching the face plate to a portion of the rear face R* of the case 2, the face plate is attached to the entire face of the rear face R* of the case 2 so that no corners are formed with the face plate.

However, according to the above configuration, users such as radiation technicians using the radiation image capturing apparatus 1 may feel that the rear face R* side of the case 2 of the radiation image capturing apparatus 1 with the name plate attached easily slips. A gripping member can be attached to the rear face R* side of the case 2. However, in this case, when the gripping member is simply attached to the rear face R* of the case 2, the corner or the edge of the gripping member may be caught by the bed or the patient's clothes while inserting the radiation image capturing apparatus 1 between the patient and the bed. This may make the procedure troublesome. Typically, the surface of the gripping member has a large friction coefficient. Therefore, when the gripping member is attached on the face plate Ra*, the face of the gripping member with the large friction coefficient comes in direct contact with the face of the bed or the patient's clothes. With this, the burden during the procedure may become heavy.

As shown in FIG. 8, a rounded rectangular cut C can be formed to take off the face plate Ra* so that the gripping member G can be attached in the predetermined position (FIG. 8 shows an example where the predetermined position is a position near the 4 sides of the case 2) of the face plate Ra* attached to the rear face R* of the case 2 of the radiation image capturing apparatus 1.

The rounded rectangular portion of the predetermined position of the face plate Ra* where the gripping member G is attached is taken off, and the gripping member G formed in the same shape as the portion is attached. FIG. 8 shows an example in which the gripping portion G is attached in 2 locations near the short side of the case 2. When the gripping member G is not attached, the radiation image capturing apparatus 1 is used in a state without taking off each portion of the rounded rectangle.

Even when the gripping member G is attached as described above, in order to prevent the surface, edge or the corner of the gripping member G from being caught by the bed or the patient's clothes, the thickness of the gripping member G is made the same or smaller than the thickness of the face plate Ra*. The gripping member G can be formed with a material with high gripping performance such as rubber. The surface of the gripping member G can be an emboss structure with a convex portion or one or a plurality of holes can be formed in the gripping member G to enhance the gripping performance. Other than the above, preferably, the gripping member G can have chemical resistance properties or scratch resistance properties, or have a structure or material so that cleaning is easy when soiled.

The gripping member G can be attached to the rear face R* of the case 2 of the radiation image capturing apparatus 1. Therefore, the operation performance (specifically, holding performance) of the radiation image capturing apparatus 1 when the radiation image capturing apparatus 1 is carried or inserted between the patient and the bed can be enhanced.

A portion of the face plate attached to the rear face R* of the case 2 of the radiation image capturing apparatus 1 is taken off to form a concave portion in the rear face R* of the case 2, and the gripping member G is attached here. Therefore, the gripping member G can be attached without projecting outside the rear face R* of the case 2. Therefore, it is possible to reliably prevent the gripping member G from being caught by the patient's clothes or the bed when the radiation image capturing apparatus 1 is inserted between the patient and the bed, and from this point also, the operation performance (in this case ease of inserting) of the radiation image capturing apparatus 1 can be enhanced.

The rounded rectangular cut C can be formed in the predetermined position of the face plate Ra* attached to the rear face R* of the case 2 of the radiation image capturing apparatus 1, and this can be taken off so that the gripping member G can be attached. Therefore, when the gripping member G is attached, the cut portion of the face plate Ra* is taken off to attach the gripping member G and the gripping member G can be easily and reliably attached to the case 2. When the gripping member G is not attached, the cut portion of the face plate Ra* is not taken off and the radiation image capturing apparatus 1 can be used in a state as is. Therefore, in either case, the radiation image capturing apparatus 1 can be reliably used, and the radiation image capturing apparatus 1 becomes easy to use for the user such as the radiation technician, etc.

According to the above description, the face plate Ra* is attached to the rear face R* of the case 2 of the radiation image capturing apparatus 1. However, the face plate does not have to be attached to the rear face R* of the case 2, and for example, a protecting thin plate or film can be attached. Moreover, the position where the gripping member G is attached can be selected freely, and the configuration is not limited to the example described above. According to the present embodiment described above, the gripping member G is attached after shipping the radiation image capturing apparatus 1 from the factory. However, the gripping member G can be attached when the radiation image capturing apparatus 1 is shipped from the factory.

[Configuration to Enhance Waterproof Performance of Case of Radiation Image Capturing Apparatus]

As described above, when the liquid such as urine, blood, etc. of the patient infiltrates into the case 2 of the radiation image capturing apparatus 1, bad influence occurs, such as the electronic component 32 and the PCB 33 on the sensor panel SP (see FIG. 2) stored in the case 2, and the battery 36 may be short-circuited or the member may be damaged or degraded. Consequently, it may not be possible to use the radiation image capturing apparatus 1.

The liquid infiltrates from the gap and the opening in the case 2 of the radiation image capturing apparatus 1. Therefore, various methods are employed to make the case 2 waterproof in the radiation image capturing apparatus 1 of the present embodiment.

[Waterproof Structure in the Portion of Protecting Cover]

For example, as shown in FIG. 5, according to the present embodiment, the inside cover 2b is inserted inside the edge portion 2A1 of the housing main body unit 2A of the case 2, and the above is covered from the outside with the protecting cover 2B to block the opening of the housing main body unit 2A (similarly applied to the protecting cover 2C side (see FIG. 1)).

However, according to such configuration, the liquid infiltrates from the gap between the protecting cover 2B and the edge portion 2A1 of the housing main body unit 2A of the case 2, the liquid passes the latched portion of the edge portion 2A1 of the housing main body unit 2A of the case 2 and the inside cover 2b, the liquid passes the gap between the edge portion 2A1 of the housing main body unit 2A and the inside cover 2b inserted therein, and the liquid infiltrates into the case 2.

As the configuration to prevent the infiltration of the liquid into the portion of the protecting cover 2B, for example, there is a configuration such as storing the entire case 2 in a waterproof bag or case. However, according to such configuration, since the bag or case has a certain thickness, the thickness of the case 2 in the radiation entering direction may not be within the range of the above described JIS standard size, in other words, 13 to 16 [mm]. When the entire case 2 is stored in a waterproof case, the weight of the radiation image capturing apparatus 1 increases in the amount of the weight of the case, etc. Therefore, there is a problem that the radiation image capturing apparatus 1 becomes heavier.

Therefore, such configuration is not always an effective method as long as the thickness of the case 2 in the radiation entering direction is made with the JIS standard size. When the thickness of the case 2 in the radiation entering direction can be made freely without the limits of the JIS standard size, the above configuration can be employed.

Another configuration may be to attach a waterproof sheet or insert packing in the opening A (see FIG. 5) between the protecting cover 2B and the edge portion 2A1 of the housing main body unit 2A of the case 2, which is the entrance of the above infiltration route of the liquid. However, the infiltration of the liquid cannot always be reliably prevented by such configuration.

Figure 9A:
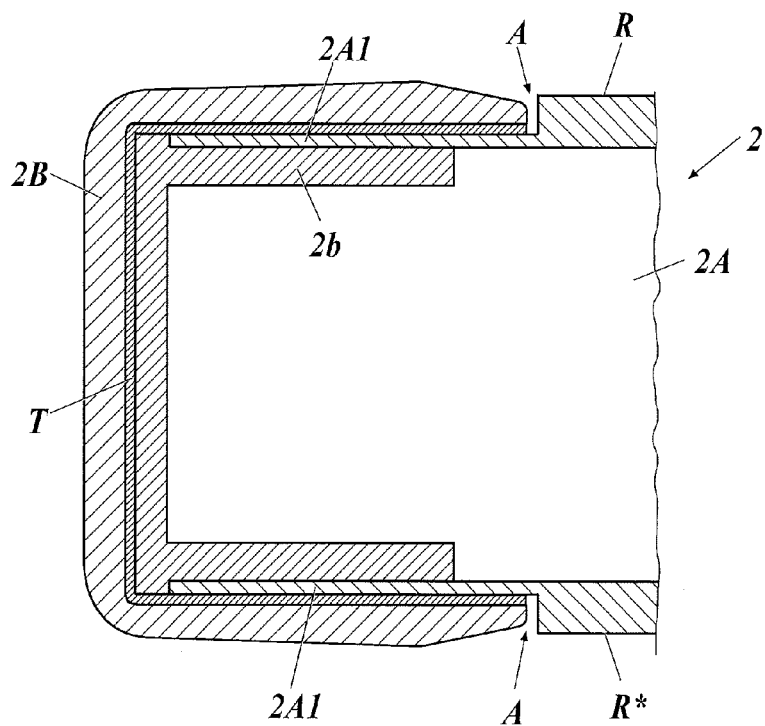
FIG. 9A is a diagram describing a waterproof structure in a portion of a protecting cover of the case of the radiation image capturing apparatus.

As shown in FIG. 9A, the inside cover 2b is inserted in the edge portion 2A1 of the housing main body unit 2A of the case 2, and the waterproof member T in a tape shape is attached from the outside to cover the above. The opening of the housing main body unit 2A can be blocked by attaching the protecting cover 2B from the outside to cover the above. FIG. 9A does not describe the ventilation hole H, the ventilation filter F and the like, but the ventilation hole H and the ventilation filter F are suitably provided according to necessity.

For example, rubber, one-sided adhesive tape, etc. can be used as the waterproof member T. However, according to the present embodiment, waterproof double-sided adhesive tape (hereinafter referred to as waterproof tape T) can be used. The waterproof tape T is attached to cover the edge portion 2A1 of the housing main body unit 2A of the case 2 and the inside cover inserted therein from the outside, and the film is attached on the outside face of the waterproof tape T. This film removes the adhesion on the protecting cover 2B side so that the protecting cover 2B can be easily fitted, and prevents soil from attaching to the surface of the waterproof tape T to enhance cleaning performance of the surface of the waterproof tape. Alternatively, the waterproof tape T on which the film is attached to one side in advance can be attached to the edge portion 2A1 of the housing main body unit 2A of the case 2 and the inside cover 2b from the outside. Then, as shown in FIG. 9A, the protecting cover 2B is attached from the outside of the waterproof tape T.

According to the configuration as described above, before the protecting cover 2B is attached to the edge portion 2A1 of the housing main body unit 2A of the case 2 and the inside cover 2b, the waterproof member such as the waterproof tape T, etc. can be attached so as to cover the above from the outside and the protecting cover 2B can be attached. With this, the waterproof member T can be easily attached to the portion of the gap between the protecting cover 2B and the edge portion 2A1 of the housing main body unit 2A of the case 2.

By attaching the waterproof member T as described above, even if the liquid such as the patient's urine infiltrates into the opening A (see FIG. 9A) between the protecting cover 2B and the edge portion 2A1 of the housing main body unit 2A of the case 2, since there is the waterproof member T, it is possible to prevent the liquid from infiltrating further inside, in other words, to reliably prevent the liquid from passing through the gap between the protecting cover 2B and the edge portion 2A1 of the housing main body unit 2A of the case 2 and infiltrating inside.

Figure 9B:
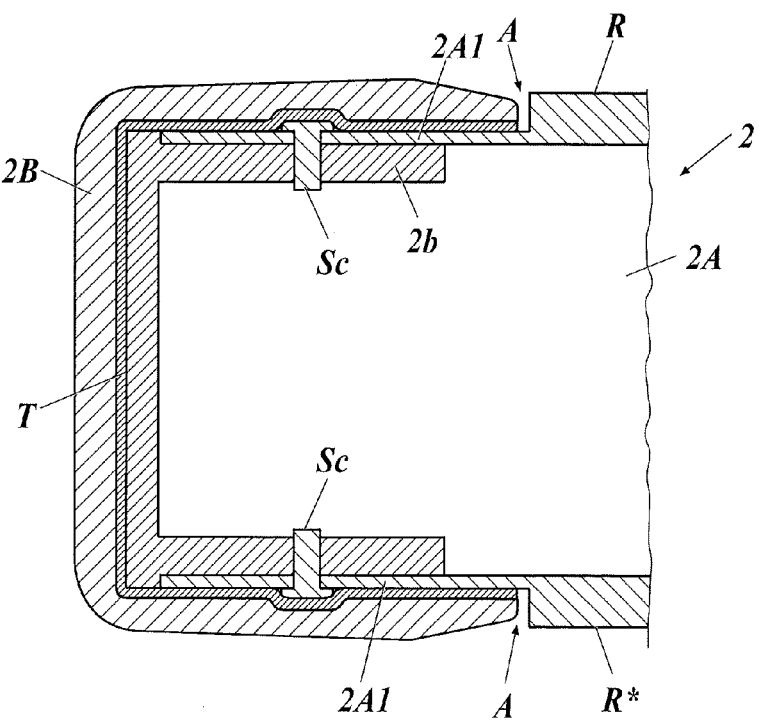
FIG. 9B is a diagram showing waterproof tape with an emboss shape made in advance is attached.

For example, as shown in FIG. 9B, when there is a convex portion such as a head of a screw Sc on the face where the waterproof tape T is attached, such as the outer face of the edge portion 2A1 of the housing main body unit 2A of the case 2 or the outer face of the inside cover 2b, it is possible to provide in advance an emboss shape in the position of the waterproof tape T corresponding to the convex portion along the projecting shape of the convex portion. By providing such emboss shape, the waterproof tape T can be attached so as to follow the shape of the convex portion on the attaching face, and the wrinkles are not formed in the waterproof tape T. Therefore, the waterproof function can be maintained.

Such emboss shape can be provided only in the waterproof tape T, and when the film is attached on the waterproof tape T, the emboss shape can be provided on both the waterproof tape T and the film. Moreover, the emboss shape can be provided on the waterproof tape T with the film attached to one face in advance. From the viewpoint of productivity in attaching, preferably, the thickness of the film attached to the waterproof tape T is 30 [μm] or more and 50 [μm] or less.

[Test to Check Waterproof Performance]

According to the present embodiment, in addition to the waterproof structure of the portion of the protecting cover 2B, the waterproof structure of the above-described ventilation hole H (see FIG. 5) provided with the above-described ventilation filter F and the later-described units of the radiation image capturing apparatus are tested by tests regarding waterproof performance to check the waterproof performance in each unit of the radiation image capturing apparatus 1.

In this case, in the test, the radiation image capturing apparatus 1 is left in a state dipped into water at a depth of 30 [mm], and applied with a load of 60 [kg] from the radiation entering face R (see FIG. 1 and FIG. 2) side for 10 minutes. Then, the load of 60 [kg] is removed. Next, it is confirmed whether water infiltrates into the case 2. When the water infiltrated inside, the location where the water infiltrated is confirmed. The load of 60 [kg] corresponds to the load applied to the radiation entering face R when a patient with a weight of 130 [kg] is lying in a state with the gluteal region placed on the radiation entering face R of the radiation image capturing apparatus 1.

In other words, such test condition is set as a condition to guarantee that liquid does not infiltrate into the case 2 for at least 10 minutes in a severe state such as the above where the patient with the above weight lies on the radiation entering face R and deforms the case 2 of the radiation image capturing apparatus 1, and a state where the radiation image capturing apparatus 1 is soaked in the patient's urine, etc.

Then, when infiltration of water into the case 2 cannot be seen under the above test condition, it is judged that the waterproof performance of the case 2 of the radiation image capturing apparatus 1 is guaranteed. The waterproof structure in the portion of the protecting cover 2B, and the waterproof structure of the configuration of the ventilation hole H provided with the ventilation filter F or the later-described units of the radiation image capturing apparatus 1 are all guaranteed to be waterproof by performing the above tests.

[Waterproof Structure in Portion Such as Switch, Etc.]

As shown in FIG. 1, the protecting cover 2B is provided with the power source switch 37, the switching switch 38, the indicator 40, etc. When such switch, indicator, etc. are provided, although illustration is omitted, usually, a hole is opened in the protecting cover 2B and the button portion of the switch projects from inside to the outside through the hole. When the indicator is provided, the emitted light of the LED, etc. inside can be seen from the hole or window provided in the protecting cover 2B.

However, according to such configuration, the liquid infiltrates into the case 2 from the portion surrounding the hole or the window provided in the protecting cover 2B. For example, therefore, it is possible to prevent the infiltration of liquid from such portions according to the configuration below.

Figure 10A:
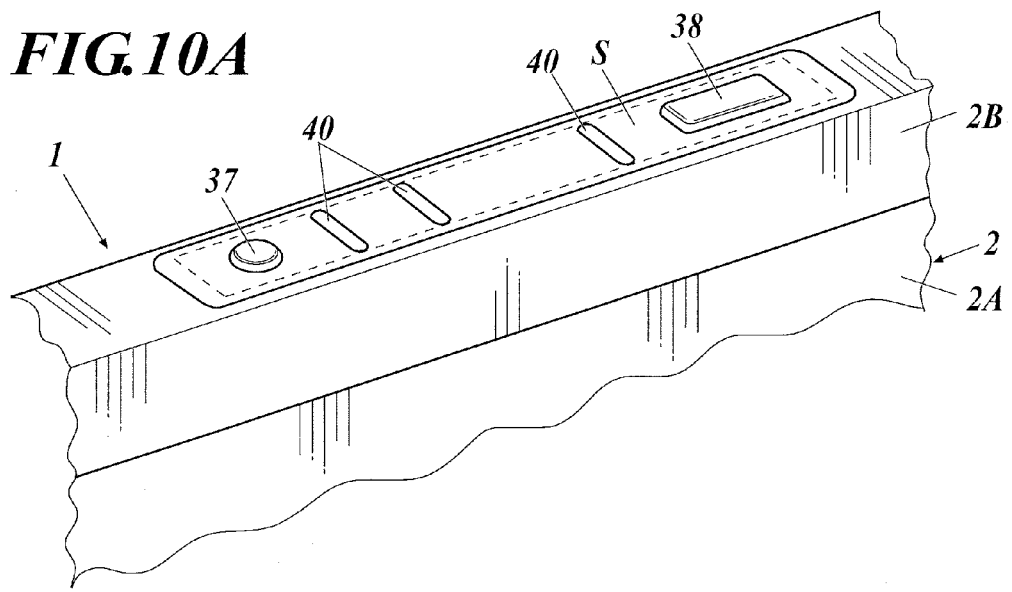
FIG. 10A is a diagram describing a waterproof structure in a portion of a switch, etc. of the case of the radiation image capturing apparatus.

Specifically, although illustration is omitted, similar to conventional examples, the substrate provided with the buttons such as the power source switch 37 and the switching switch 38 and the LED composing the indicator 40 is attached to the above described inside cover 2b (see FIG. 9A, etc.). As shown in FIG. 10A, an opening (see broken line in drawing) is provided in advance in the position corresponding to the protecting cover 2B. When the inside cover 2b with the substrate attached is attached to the edge portion 2A1 of the housing main body unit 2A of the case 2 and the protecting cover 2B is attached so as to cover the above, although illustration is omitted in FIG. 10A, the buttons and the LED, etc. attached to the substrate are exposed outside through the opening of the protecting cover 2B.

Then, as shown in FIG. 10A, in this state, the waterproof sheet S such as an emboss sheet provided with convex portions in the position corresponding to the button and the LED is attached from the outside to the protecting cover 2B so as to block the opening of the protecting cover 2B. Alternatively, the waterproof sheet S can be attached from inside of the protecting cover 2B. With either method, the waterproof sheet S prevents the liquid from infiltrating into the case 2 from the opening provided in the protecting cover 2B. Here, the portion of the waterproof sheet S corresponding to the indicator 40 is transparent or translucent, and the light emitted from the LED inside can be viewed.

According to such configuration, it is possible to reliably prevent the liquid from infiltrating into the case 2 from the portion of the protecting cover 2B corresponding to the power source switch 37, the switching switch 38, the indicator 40, etc. with the waterproof sheet S. Since the configuration is to simply attach the waterproof sheet S, it is possible to easily prevent the liquid from infiltrating into the case 2 from the portion of the protecting cover 2B.

On the inner side of the protecting cover 2b, the waterproof tape T as shown in FIG. 9A is attached so as to cover the substrate (hereinafter simply referred to as LED substrate) provided with buttons, LED, etc. and attached to the inside cover 2b. With this, it is possible to prevent the water attaching to the LED substrate and the liquid infiltrating inside the apparatus through the opening (see broken line in FIG. 10A) opened in the inside cover 2b.

Figure 10B:
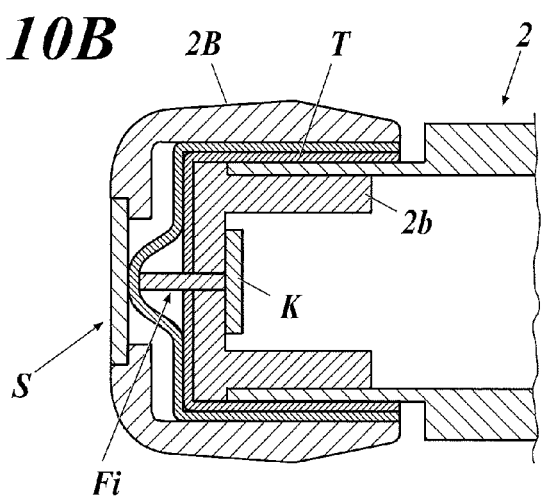
FIG. 10B is a diagram describing a modification in which double-sided tape of the waterproof tape is removed in only a range surrounding an LED substrate and there is only film.

In this case, when there is a waterproof tape T to cover the entire LED substrate, if the waterproof tape T is not transparent, there may be a problem that the passing of the light of the LED is blocked by the waterproof tape T. When the thickness of the waterproof tape T is thick, there may be a bad influence to the feel of pressing the button. For example, as shown in FIG. 10B, the configuration can be made so that there is no double-sided tape of the waterproof tape T in the range covering the LED substrate K and there is only film Fi.

According to such configuration, the light of the LED can pass through the film Fi and the feel of pressing the button can become preferable. The film Fi can have a projecting emboss shape along the height of the button component in the portion of the button on the LED substrate K. If the film Fi is formed flat without forming the emboss shape, the button may be pressed by the tension of the flat film face. However, when the emboss shape is formed in the portion of the button of the film Fi as described above, this prevents the film Fi from pressing the button. In addition to the above, it is possible to make the feel of pressing the button preferable.

[Waterproof Structure in Portion of Connector]

As shown in FIG. 1, a connector 39 is provided in the case 2 of the radiation image capturing apparatus 1, and the liquid may infiltrate into the case 2 from the portion of the connector 39. Therefore, it is possible to prevent the infiltration of the liquid from the connector 39 portion by using the packing.

Figure 11:
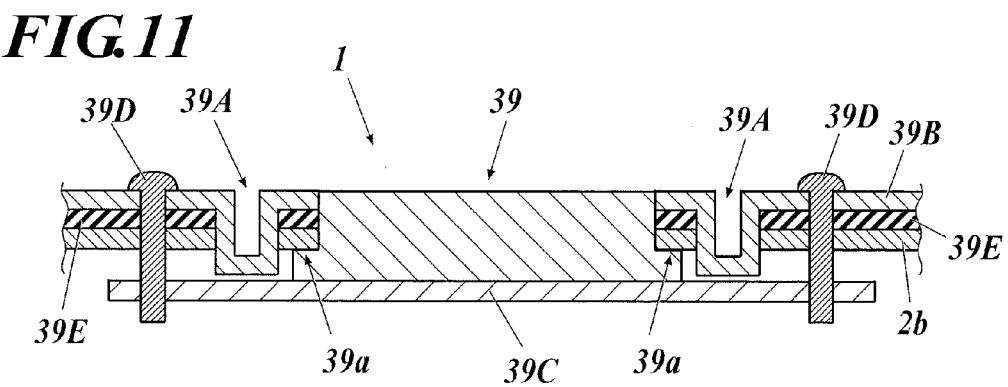
FIG. 11 is a diagram describing a waterproof structure in a portion of a connector of the case of the radiation image capturing apparatus.

According to the radiation image capturing apparatus 1 of the present embodiment, a concave portion 39A is provided for positioning near the connector 39 as shown in FIG. 11 to reliably connect an external connector such as a connector 51b of the bucky apparatus 51 (see FIG. 4) to the connector 39 of the radiation image capturing apparatus 1 when the external connecter is connected to the connector 39. A projecting portion (not shown) is provided in the external connecter, and when the connection is made, the projecting portion of the external connecter is inserted in the concave portion 39A of the connector 39 of the radiation image capturing apparatus 1. Therefore, the external connector can be positioned with respect to the connector 39 of the radiation image capturing apparatus 1 and suitably connected. According to the present embodiment, the concave portion 39A for positioning is depressed in a predetermined position of the guiding plate 39B to be formed as one with the guiding plate 39B.

An opening is provided in a predetermined location of the inside cover 2b, and as shown in FIG. 11, the connector 39 is fitted from the inside in the opening for the connector. Moreover, the concave portion 39A of the guiding plate 39B is fitted in the opening for the concave portion from the outside. Then, the guiding plate 39B is screwed to the supporting plate 39C positioned on the inner side of the connector 39 with the screw 39D. With this, the connector 39 is fixed in a position pressed to the inside cover 2b.

As shown in FIG. 11, packing 39E such as rubber is placed between the guiding plate 39B and the inside cover 2b and the above are tightened with the screw 39D. With this, the infiltration of the liquid from the portion of the connector 39 can be reliably prevented. The portion where the connector 39 is latched to the inside cover 2b (see 39a of FIG. 11) and the portion between the screw 39D and the guiding plate 39B are suitably made waterproof with packing, sealing material and waterproof tape. The portion between the guiding plate 39A and the protecting cover 2B not illustrated in FIG. 11 (see FIG. 9A, etc.) is also suitably made waterproof with the packing, sealing material, and waterproof tape, etc.

According to such configuration, the infiltration of the liquid into the case 2 from the portion of the connector 39 can be reliably prevented with the packing 39E. Since the above configuration is simply screwed together with the screw 39D in a state with the packing 39E in between, the liquid infiltrating into the case 2 from the portion of the connector 39 can be easily prevented.

[Structure of Corner of Case]
[Configuration of Portion of Edge of Protecting Cover]

In the 4 corners of the case 2 of the radiation image capturing apparatus 1, there are no structures such as switches, etc. (in other words, power source switch 37, switching switch 38, indicator 40, etc.) and the connector 39, etc., and an opening (see broken line shown in FIG. 10A) is not provided in the protecting cover 2B. Therefore, the opening provided in the protecting cover 39 does not need to be blocked with the waterproof sheet S (see FIG. 10A) and packing 39E (see FIG. 11) as in the waterproof structure of the portion such as the switch or the waterproof structure in the portion such as the connector.

According to the present embodiment, the corner of the case 2 of the radiation image capturing apparatus 1 has a special structure as described below in order to prevent damage to the sensor panel SP (see FIG. 2) in the case 2 due to dropping the radiation image capturing apparatus 1 and applying vibration and shock when the corner of the case 2 hits the floor. Because of the above special configuration, the liquid may infiltrate into the case 2 from the corner of the case 2. Therefore, suitable waterproof measures need to be taken when such configuration is employed.

Figure 12A:
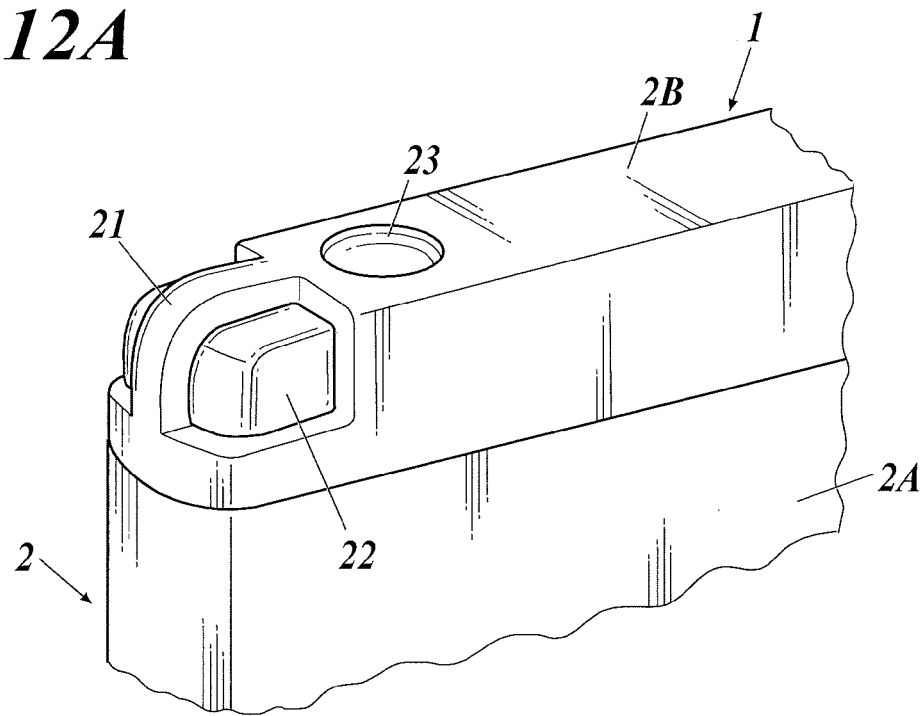
FIG. 12A is a perspective view showing an external appearance of a corner portion of the case of the radiation image capturing apparatus.
Figure 12B:
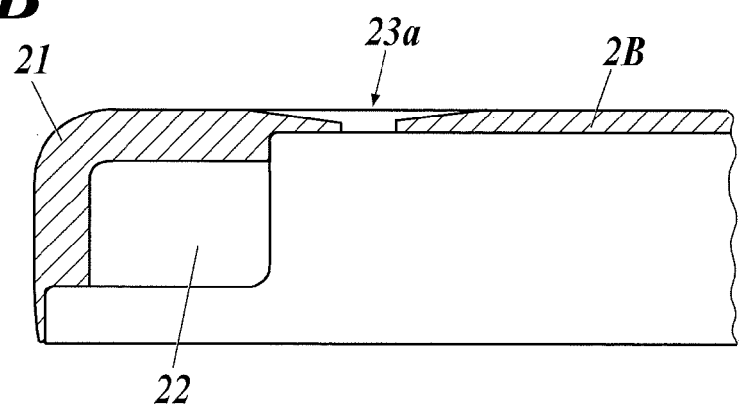
FIG. 12B is a cross-sectional view of an edge portion of a protecting cover.

The configuration of the corner of the case 2 in the radiation image capturing apparatus 1 of the present embodiment is described. The protecting cover 2B is described below, and the description of the protecting cover 2C (see FIG. 1) is omitted, but the protecting cover 2C has a similar configuration. FIG. 12A is a perspective view showing an outer appearance of the corner of the case of the radiation image capturing apparatus. FIG. 12B is a cross-sectional view of the edge of the protecting cover.

According to the present embodiment, as shown in FIG. 12A and FIG. 12B, one ridge shaped convex portion 21 is provided extending in the length direction of the protecting cover 2B in the corner of the edge of the protecting cover 2B corresponding to the corner portion of the case 2.

When such ridge shaped convex portion 21 is provided in the edge of the protecting cover 2B which is the corner of the case 2 of the radiation image capturing apparatus 1, for example, when the radiation image capturing apparatus 1 is dropped and the corner of the case 2 hits the floor, the portion of the ridge shaped convex portion 21 at the edge of the protecting cover 2B is damaged by the shock. Some of the energy of the shock of hitting the floor is absorbed by the ridge shaped convex portion 21 of the protecting cover 2B being damaged.

Therefore, since the energy applied to the case 2 of the radiation image capturing apparatus 1 from hitting the floor is reduced, the shock and the vibration applied to the sensor panel SP (see FIG. 2) in the case 2 when the radiation image capturing apparatus 1 is dropped can be reduced. Therefore, it is possible to reliably prevent the sensor panel SP from being damaged due to dropping the radiation image capturing apparatus 1.

If the portion of the edge of the protecting cover 2B which is the corner of the case 2 is not damaged when the radiation image capturing apparatus is dropped, the energy of the shock received by the portion is transmitted to the case 2 and the sensor panel SP (see FIG. 2) and the sensor panel SP is damaged. Therefore, the energy of the shock of dropping needs to be absorbed by damaging the portion of the edge of the protecting cover 2B when the radiation image capturing apparatus 1 is dropped.

However, if the portion of the edge of the protecting cover 2B is easily damaged when the radiation image capturing apparatus 1 is dropped, the portion of the edge of the protecting cover 2B cannot adequately absorb the energy of the shock of the drop. As a result, the energy of the shock of the drop is transmitted to the case 2 as is and transmitted to the sensor panel SP. Therefore, the portion of the edge of the protecting cover 2B needs to be formed with strength to a certain degree to cope with deforming by the shock of dropping, and the radiation image capturing apparatus 1 needs to be configured so that the energy from dropping is suitably absorbed.

As a result of research by the inventors of the present invention, the inventors found that it is preferable to provide the ridge shaped convex portion 21 as shown in FIG. 12A and FIG. 12B in the edge of the protecting cover 2B which is the corner of the case 2 of the radiation image capturing apparatus 1. The width and the thickness of the portion of the ridge shaped convex portion 21 is adjusted so that the easiness of damage (or the difficulty of damage) of the portion of the edge of the protecting cover 2B when the radiation image capturing apparatus 1 is dropped and the efficiency of absorbing the energy of the shock of the drop at the portion of the edge of the protecting cover 2B can be adjusted.

As shown in FIG. 12A, in order to form the ridge shaped convex portion 21 in the edge of the protecting cover 2B, the portion other than the ridge shaped convex portion 21 is formed in a concave shape. Therefore, the portion of the edge of the protecting cover 2B is convex toward the inner side (see FIG. 12B), but the concave shaped portion 22 other than the ridge shaped convex portion 21 (in other words, the portion convex toward the inner side) and the surrounding portion can be formed thicker than the thickness of the other portion of the protecting cover 2B.

When the concave shaped portion 22 other than the ridge shaped convex portion 21 and the portion near the above is formed thick, it is possible to make the strength of the portion of the edge of the protecting cover 2B stronger to cope with the deforming due to the shock of the dropping. By adjusting the thickness of this portion, it is possible to adjust the easiness of damage of the portion of the edge of the protecting cover 2B when the radiation image capturing apparatus 1 is dropped or the efficiency of absorbing the energy of the shock of the drop at the portion of the edge of the protecting cover 2B.

Figure 13A:
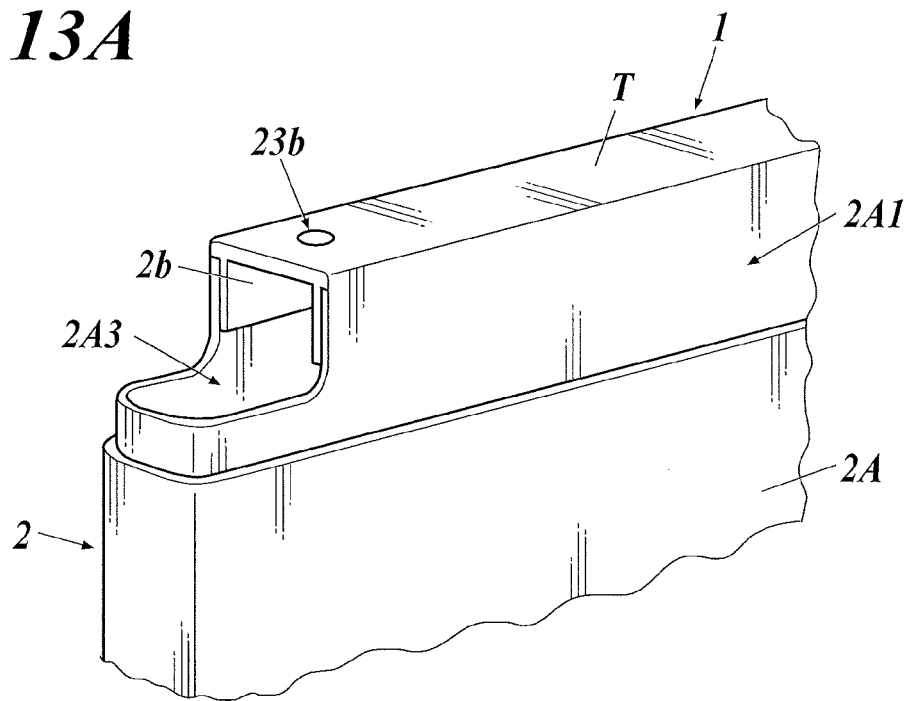
FIG. 13A is a perspective view showing a cutout portion provided in a corner portion of an edge portion of the housing main body unit.
Figure 13B:
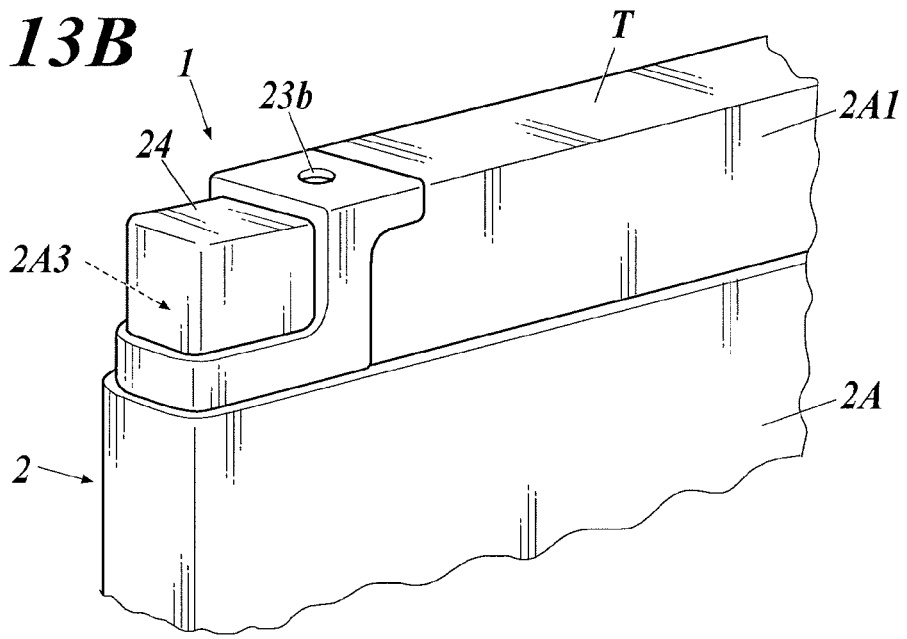
FIG. 13B is a perspective view showing a waterproof cap attached to the cutout portion.

Only one ridge shaped convex portion 21 of the edge of the protecting cover 2B can be formed as shown in FIG. 12A, etc. Alternatively, a plurality of ridge shaped convex portions 21 can be provided parallel or a plurality of ridge shaped convex portions 21 can be provided intersecting in a waffle shape. Reference numeral 23 shown in FIG. 12A represents the screw to screw the protecting cover 2B to the inside cover 2b (not shown, see FIG. 5 and FIG. 9A). Reference numerals 23a in FIGS. 12B and 23b in later described FIG. 13A and FIG. 13B represent a screw hole for the screw 23. When the screw 23 is screwed, waterproof measures such as packing or sealing material are provided in order to prevent the liquid from infiltrating from the above portion.

[Structure of Corner of Housing Main Body Unit]

When the ridge shaped convex portion 21 is formed so that it can be damaged in the portion of the edge of the protecting cover 2B, as described in FIG. 9A, according to the configuration in which the edge portion 2A1 of the housing main body unit 2A of the case 2 is covered at the portion of the edge of the protecting cover 2B from the outside, the edge portion 2A1 of the housing main body unit 2A becomes very near the ridge shaped convex portion 21 of the protecting cover 2B.

However, according to such configuration, even if the edge of the protecting cover 2B is damaged from the shock of dropping the radiation image capturing apparatus 1 and the corner of the case 2 hitting the floor, the shock is also applied to the edge portion 2A1 of the housing main body unit 2A. Then, the shock is transmitted to the entire housing main body unit 2A from the edge portion 2A1, and as a result, the case 2 and the sensor panel SP stored in the case 2 receives a great shock.

Therefore, in addition to forming the portion of the edge of the protecting cover 2B so that the portion can be damaged, as shown in FIG. 13A, the edge portion 2A1 of the housing main body unit 2 of the portion of the corner of the case 2 is cut and a cutout portion 2A3 is provided. Although illustration is omitted, when the protecting cover 2B is attached to the edge portion 2A1 of the housing main body unit 2A, the portion 22 (see FIG. 12B) in a convex toward the inner side of the edge of the protecting cover 2B is positioned in the cutout portion 2A3 of the edge portion 2A1 of the corner of the housing main body unit 2A. Therefore, the portion 22 which is convex toward the inner side of the edge of the protecting cover 2B and the edge portion 2A1 of the housing main body unit 2A do not interfere with each other.

According to FIG. 13A, the inside cover 2b is inserted in the edge portion 2A1 of the housing main body unit 2A of the case 2 of the radiation image capturing apparatus 1, and the tape shaped waterproof member T is attached so as to cover the above from the outside. The illustration of the protecting cover 2B is omitted.

[Waterproof Structure in Cutout Portion of Housing Main Body Unit]

As described above, the radiation image capturing apparatus 1 of the present embodiment has a special structure in which a ridge shaped convex portion 21 is provided in the corner of the case 2, in other words, the portion of the edge of the protecting cover 2B (see FIG. 12A and FIG. 12B) and a cutout portion 2A3 in the edge portion 2A1 of the corner of the housing main body unit 2A of the case 2 (see FIG. 13A) so that the sensor panel SP in the case 2 is not damaged by the shock or vibration of the radiation image capturing apparatus 1 being dropped and the corner of the case 2 hitting the floor.

When the cutout portion 2A3 is provided in the edge portion 2A1 of the corner of the housing main body unit 2A of the case 2, the liquid can infiltrate into the case 2 through the cutout portion 2A3. Therefore, a configuration to make the cutout portion 2A3 waterproof is necessary.

According to the present embodiment, for example, as shown in FIG. 13B, in order to seal the cutout portion 2A3 of the corner of the housing main body unit 2A, a waterproof cap 24 is attached to the cutout portion 2A3.

In this case, the waterproof cap 24 can be formed with a soft resin such as thermoplastic polyurethane (TPU). For example, when only the ridge shaped convex portion 21 (see FIG. 12A and FIG. 12B) is provided in the portion of the edge of the protecting cover 2B as described above, the energy of the shock when the case 2 hits the floor may not be sufficiently absorbed. In this case, the waterproof cap 24 can be formed with a material having a certain degree of strength to cope with deforming due to the shock of dropping, examples including metal.

As described above, according to the present embodiment, the film is attached to the face on the outer side of the double sided tape (waterproof member T) attached to cover the edge portion 2A1 of the housing main body unit 2A and the inside cover 2b from outside so that the protecting cover 2B can be easily fit. In the portion where the waterproof cap 24 is attached, the film can be removed and the waterproof cap 24 can be attached on the face on the outer side of the double sided tape (waterproof member T). Alternatively, the double sided tape can be removed in this portion to expose the edge portion 2A1 of the housing main body unit 2A and the waterproof cap 24 can be adhered to the exposed edge portion 2A1, etc. Alternatively, the waterproof cap 24 can be adhered from above the film attached to the face on the outer side of the double sided tape (waterproof member T).

According to the above configuration, even if a cutout portion 2A3 is provided in the edge portion 2A1 of the housing main body unit 2A so that the shock when the radiation image capturing apparatus 1 is dropped is not directly transmitted to the housing main body unit 2A of the case 2, the cutout unit 2A3 is sealed with the waterproof cap 24. Therefore, it is possible to reliably prevent the liquid from infiltrating into the case 2 from the cutout portion 2A3.

As described above, for example, when the waterproof cap 24 (see FIG. 13B) is formed from metal, since the metal is hard, if the case 2 hits the floor and the corner of the protecting cover 2B (see FIG. 12A, FIG. 12B, etc.) is deformed to the inner side, the shock when the corner of the protecting cover 2B and the waterproof cap 24 on the inner side hits each other is transmitted to the case 2, and this may also be transmitted to the sensor panel SP (see FIG. 2) in the case 2. Alternatively, the corner of the protecting cover 2B may be deformed to the inner side and the waterproof cap 24 may also be deformed by being pushed to the inner side with the corner of the protecting cover 2B. With this, the adhesive that adheres the waterproof cap 24 and the case 2 may be removed and the waterproof performance may reduce.

When the waterproof cap 24 is formed with a soft resin as described above, if the corner of the protecting cover 2B is pushed to the inner side when the case 2 hits the floor, the waterproof cap 24 may be damaged by the shock.

Figure 14:
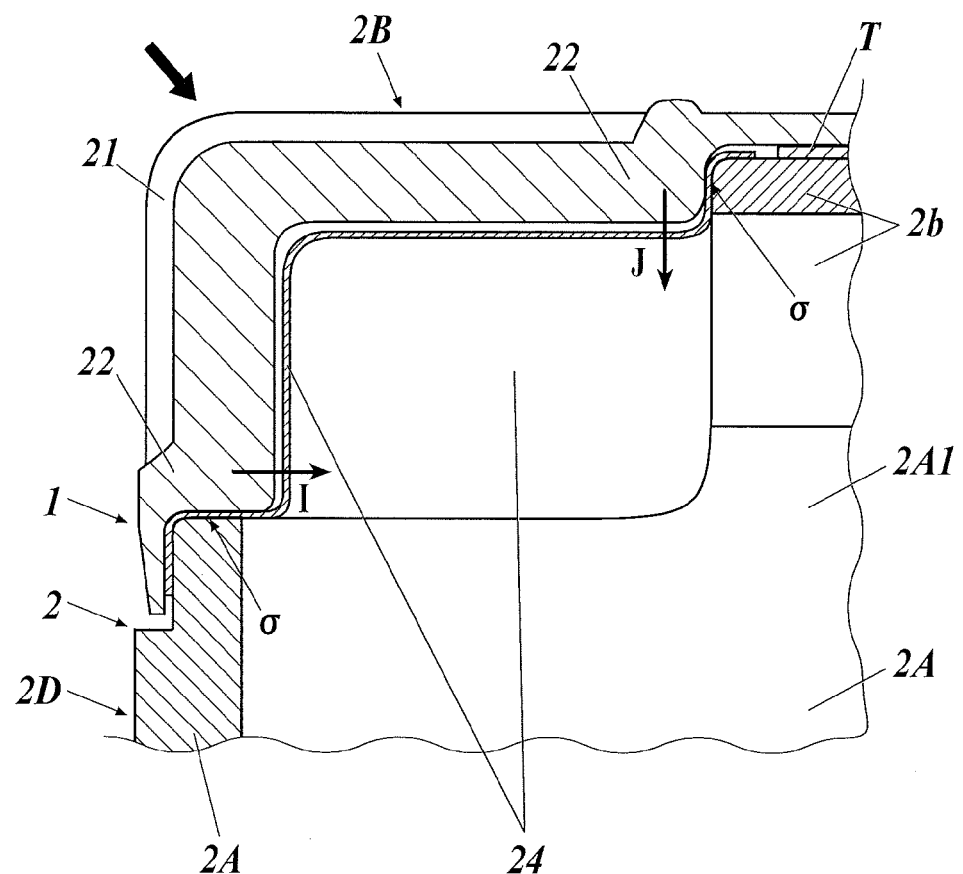
FIG. 14 is a cross-sectional view showing a state where the waterproof cap is attached and the protecting cover is fitted in the cutout portion of the housing main body unit of the case.

In other words, when the waterproof cap 24 formed with soft resin is attached so as to seal the opening of the cutout portion 2A3 provided in the edge portion 2A1 of the housing main body unit 2A of the case 2 as shown in FIG. 13B and the protecting cover 2B is fitted to cover the above from the outside as shown in FIG. 12A and FIG. 12B, as shown in the bottom left of the cross-sectional view shown in FIG. 14, the portion of the edge σ of the waterproof cap 24 is placed between the portion 22 convex to the inner side of the protecting cover 2B and the side face 2D of the case 2 or as shown in the top right of the cross-sectional view shown in FIG. 14, the portion of the edge σ of the waterproof cap 24 is placed between the portion 22 convex to the inner side of the protecting cover 2B and the inside cover 2b and the edge portion 2A1 of the housing main body unit 2A.

When the case 2 hits the floor in this state and a strong force is applied to the corner of the protecting cover 2B as shown with a thick arrow in FIG. 14, the portion of the edge σ of the waterproof cover 24 is held with a strong force between the protecting cover 2B and the side face 2D of the case 2, the inside cover 2b, etc. Therefore, the waterproof cap 24 (specifically, the portion of the edge σ) which is formed with soft resin, etc. may be damaged and the waterproof performance may be lost.

Figure 15A:
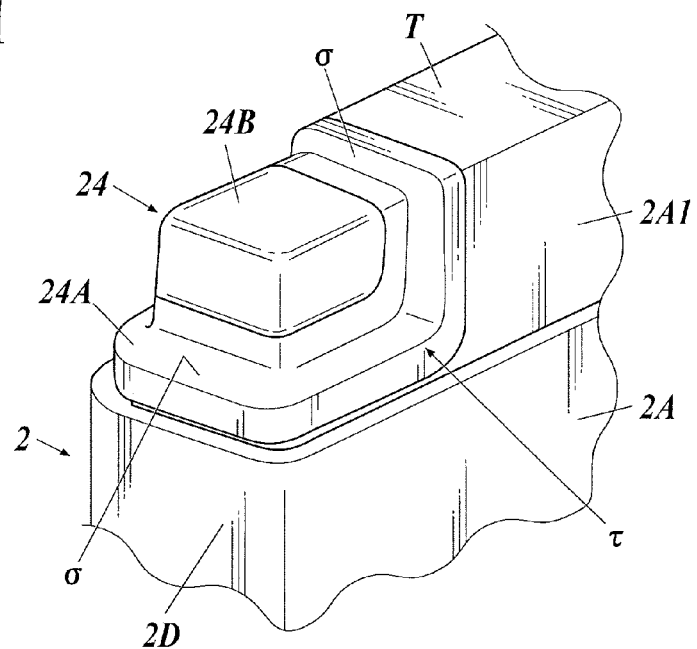
FIG. 15A is a perspective view showing a waterproof cap formed with metallic material in a periphery portion and soft material in a center portion.

Therefore, as shown in FIG. 15A, the periphery portion 24A including the edge σ between the protecting cover 2B (not shown in FIG. 15) and the side face 2D of the case 2, the inside cover 2b, etc. can be formed with metallic material, and the center portion 24B which is pressed by the protecting cover 2B when strong force is applied to the protecting cover 2B can be formed with a soft material such as soft resin.

According to the above configuration, even if the portion of the edge σ of the waterproof cap 24 is placed between the protecting cover 2B and the side face 2D of the case 2, the inside cover 2b, etc., the portion is formed with the metallic material. Therefore, the portion is hardly damaged. When the corner of the protecting cover 2B (see FIG. 15B, etc.) is deformed to the inner side when the case 2 hits the floor, the center portion 24B of the waterproof cap 24 formed with the soft material is pressed by the corner of the protecting cover 2B deformed to the inner side. Therefore, it is possible to make a configuration so that the shock is not transmitted to the case 2 and the sensor panel SP inside the case 2 even if the protecting cover 2B hits the center portion 24B of the waterproof cap 24.

However, even if the waterproof cap 24 is formed as shown in FIG. 15A, when the case 2 hits the floor and a strong force is applied to the corner of the protecting cover 2B, if the periphery portion 24A (in other words, the portion of the edge σ) of the waterproof cap 24 formed with the metallic material is held with a strong force between the protecting cover 2B and the side face 2D of the case 2, inside cover 2b, etc., the possibility of damage is not completely lost.

When the entire waterproof cap 24 is formed with metal as shown in FIG. 14, if a strong force is applied to the corner of the protecting cover 2B, in addition to the force applied to the waterproof cap 24 by being held between the components, a force pressing to the right side as shown with the arrow I in the diagram is applied to the portion where the protecting cover 2B comes into contact with the waterproof cover 24 and the side face 2D of the case 2. Moreover, in addition to the force applied to the waterproof cap 24 by being held between the components, a force pressing downward as shown with the arrow J in the diagram is applied to the portion where the protecting cover 2B comes into contact with the waterproof cover 24 and the inside cover 2b as shown in the top of FIG. 14. Therefore, as a result, there is a force to expand the periphery portion 24A of the waterproof cap 24 outward. As a result, as described above, the adhesive adhering the waterproof cap 24 and the case 2 may be removed, and the waterproof performance may be lost.

Such situation occurs similarly when the periphery portion 24A of the waterproof cap 24 is formed with the metallic material as shown in FIG. 15A. When a strong force is applied to the corner of the protecting cover 2B, the force in the direction as shown with the arrows I and J in FIG. 14 is applied to the periphery portion 24A of the waterproof cap 24. As a result, there is a force applied outward expanding the portion shown with τ in FIG. 15 in the periphery portion 24A of the waterproof cap. Therefore, the adhesion between the waterproof cap 24 and the edge portion 2A1 of the housing main body unit 2A is separated in the portion of the τ of the periphery portion 24A of the waterproof cap 24, and the waterproof performance may be lost in this portion.

In the portion shown in the bottom left of the cross-sectional view of FIG. 14, the edge of the side face 2D of the case 2 (upper edge in FIG. 14) and the portion of the edge σ of the waterproof cap 24 fixed to this portion is formed in a normal direction of the side face 2D of the case 2. Alternatively, instead of the above, as shown in the bottom left of the cross-sectional view of FIG. 15B, the configuration can be formed so that the edge of the side face 2D of the case 2 and the periphery portion 24A of the waterproof cap 24 fixed to this portion (in other words, portion of the edge σ) is diagonal with respect to the normal direction of the side face 2D of the case 2.

Figure 15B:
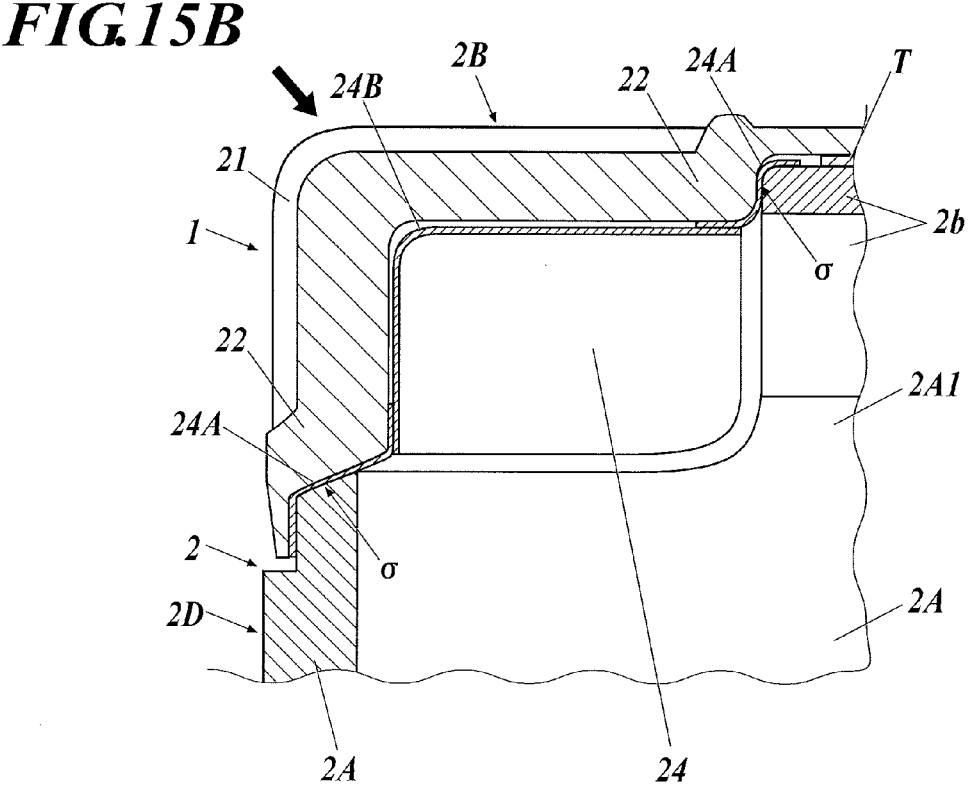
FIG. 15B is a cross-sectional view showing a state forming the edge portion of the housing main body unit of the case and the periphery portion of the waterproof cap diagonally.

According to the above configuration, when the case 2 hits the floor and a strong force is applied to the corner of the protecting cover 2B as shown with the thick arrow in FIG. 15B, since the edge of the side face 2D of the case 2 and the periphery portion 24A of the waterproof cap 24 is diagonal, there is a force so that the protecting cover 2B escapes outside in the portion of the periphery portion 24A of the waterproof cover 24 shown in the bottom left of the cross-ssectional view of FIG. 15B (in other words, portion of the edge σ). Alternatively, at least the force moving the protecting cover 2B toward the inner side (see arrow I of FIG. 14 as described above) becomes weak, and it is possible to prevent damage in the periphery portion 24A of the waterproof cap 24 (in other words, the portion of the edge σ).

The tilt provided in the periphery portion 24A of the waterproof cap 24 and the edge of the side face 2D of the case 2 can be formed in portions such as the portion of the edge σ at the upper right of the cross-sectional view shown in FIG. 15B. Moreover, the tilt can be formed in the entire periphery portion 24A of the waterproof cap 24.

According to the above configuration, when the case 2 hits the floor and a strong force is applied to the corner of the protecting cover 2B, instead of the periphery portion 24A of the waterproof cap 24 spreading outward, the protecting cover 2B shifts to the outer side. Therefore, it is possible to reliably prevent the periphery portion 24A of the waterproof cap 24, specifically the portion shown with τ in FIG. 15A from spreading outward. Consequently, it is possible to prevent the waterproof performance from being lost.

[Configuration to Prevent V-Shaped Fracture of Sensor Substrate]

As described above, when the radiation image capturing apparatus 1 is dropped and the corner of the case 2 hits the floor, the shock and the vibration may be transmitted to the sensor panel SP in the case 2 (see FIG. 2), and the sensor panel SP may be damaged. The configuration (in other words, the ridge shaped convex portion 21 in the protecting cover 2B) to prevent the above is described above.

As described above, the sensor panel SP may be damaged when the radiation image capturing apparatus 1 is dropped. Other than the above, the sensor panel SP may be damaged, for example, when a local force is applied to the radiation entering face R, etc. of the radiation image capturing apparatus 1. This may occur when a patient transported on a stretcher is roughly laid on the radiation image capturing apparatus 1 on a bed and a strong force is applied to the radiation entering face R of the radiation image capturing apparatus 1 by the patient's gluteal region.

Figure 17A:
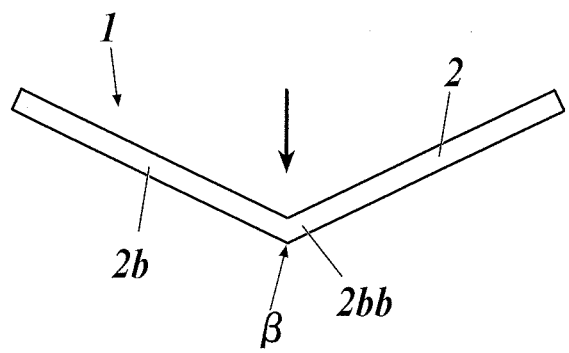
FIG. 17A is an image diagram showing the center portion of the case of the radiation image capturing apparatus folded in a V-shape when strong force is applied locally.

When a local strong force is applied to the center portion of the radiation entering face R of the case 2 of the radiation image capturing apparatus 1, the force may be applied so that the case 2 and the sensor panel SP inside is bent in a V shape (see later described FIG. 17A). When such force is applied to the sensor panel SP, the sensor substrate 4 and the scintillator substrate 34 (see FIG. 2) composed of the glass substrate is fractured in a V-shape. Therefore, the sensor panel SP may be damaged when a force that bends the case 2 of the radiation image capturing apparatus 1 in a V shape is applied.

As shown in FIG. 1, for example, as shown in the side of one protecting cover 2C composing the case 2 of the radiation image capturing apparatus 1, the antenna 41 (see FIG. 4) may be provided in the portion β in the substantial center of the protecting cover 2C in the longitudinal direction. In order to provide the antenna 41 inside the case 2, the antenna 41 may be provided inside the inside cover 2b (see FIG. 5 and FIG. 9A).

In this case, if the inside cover 2b is formed with metal such as magnesium (Mg), aluminum (Al), etc. as described above, the antenna 41 cannot transmit and receive radio waves due to the metallic inside cover 2b. Therefore, as shown in FIG. 16, in the inside cover 2b, the portion 2ba other than the portion where the antenna 41 is provided is formed with metal such as magnesium, etc. and the portion 2bb where the antenna 41 is provided is formed with resin, etc. and the 2 metallic portions 2ba and the 1 portion 2bb formed with resin, etc. are connected to form the inside cover 2b.

Figure 16:
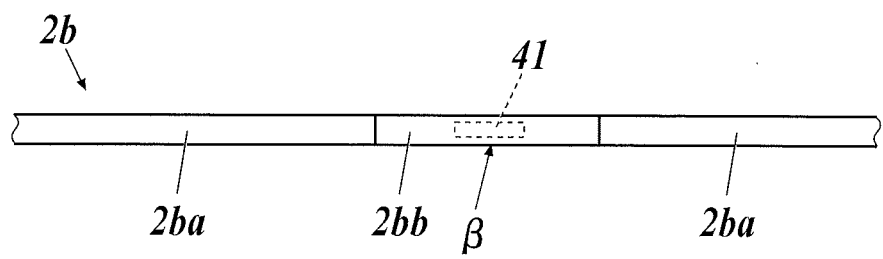
FIG. 16 is a diagram showing an inside cover formed by connecting three portions.

However, when the inside cover 2b is formed with 3 pieces as shown in FIG. 16, the portion 2bb of the inside cover 2b formed with resin, etc. and the connecting portion between the portions 2ba and 2bb become relatively weak. For example, as described above, when the patient is laid roughly on the radiation image capturing apparatus 1 and a strong local force is applied to the center of the radiation entering face R of the case 2 of the radiation image capturing apparatus 1, as shown as an image in FIG. 17A, the case 2 is easily bent in a V shape in the portion with weak strength. As described above, a V-shaped fracture occurs in the glass substrate of the sensor substrate 4 and the scintillator 34, etc., and the sensor panel SP is damaged.

Instead of the three piece structure as shown in FIG. 16C, the inside cover 2b can be formed as one with, for example, fiber reinforced plastic. In this case, if carbon fiber reinforced plastic (CFRP) is used, the transmitting and receiving of the radio wave by the antenna 41 is blocked with the carbon fiber. Therefore, preferably, glass fiber reinforced plastic (GFRP) is used.

Figure 17B:
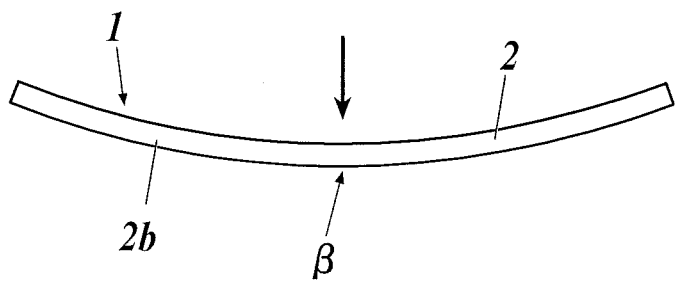
FIG. 17B is an image diagram showing the center portion of the case of the radiation image capturing apparatus bending entirely when strong force is applied locally.

When the inside cover 2b is formed as one (in other words, without dividing into 3 pieces) with glass fiber reinforced plastic, even if the patient is roughly laid on the radiation image capturing apparatus 1 and strong force is applied locally to the center portion of the radiation entering face R of the case 2 of the radiation image capturing apparatus 1, as shown as an image in FIG. 17B, the entire inside cover 2b bends and the force spreads. Therefore, the entire sensor panel SP in the case 2 of the radiation image capturing apparatus 1 bends, the force is not applied locally and the force spreads throughout the entire panel. With this, it is possible to reliably prevent the V-shaped fracture from occurring in the glass substrate of the sensor substrate 4 and the scintillator substrate 34, etc.

The following test to see the deforming amount [mm] of the center portion (portion β shown in FIG. 1) of the case 2 was performed by the inventors of the present invention. A load applied to the center portion of the case 2 without support from below is changed with only both edges of the case 2 of the radiation image capturing apparatus 1 in the longitudinal direction (in other words, 2 short sides of the case 2 where the protecting covers 2B and 2C are not attached) supported from below. Compared to the deforming amount of the case 2 when the inside cover 2b is formed with 3 pieces as shown in FIG. 16, the deforming amount of the case 2 when the inside cover 2b is formed as one with glass fiber reinforced plastic is smaller by about 1/3.3 times.

In other words, when a load which makes the deforming amount of the case 2 including the inside cover 2b formed with 3 pieces to 10 [mm] is applied as a load on the center portion of the case 2 including the inside cover formed as one with glass fiber reinforced plastic, the deforming amount is only about 3 [mm].

As described above, in an apparatus where the inside cover 2b is formed as one with fiber reinforced plastic such as glass fiber reinforced plastic, when the force is applied locally to the case 2, the entire inside cover 2b bends and the force is able to reliably spread. With this, the entire sensor panel SP bends. Therefore, it is possible to reliably prevent the V-shaped fracture in the glass substrate of the sensor substrate 4 and the scintillator substrate 34.

The present invention is not limited to the above-described embodiments, and the present invention can be suitably modified without leaving the scope of the present invention.

The present U.S. patent application claims priority under the Paris Convention of Japanese Patent Application No. 2014-079978 filed on Apr. 9, 2014 and Japanese Patent Application No. 2014-249514 filed on Dec. 10, 2014 the entirety of which is incorporated herein by reference.

What is claimed is:
1. A radiation image capturing apparatus comprising:
  a sensor panel which includes a plurality of radiation detecting elements aligned two-dimensionally; and
  a case which stores the sensor panel, the case comprising:
    an inner case including an inner case hole;
    a protective cover disposed over the inner case including a protective cover hole, the inner case hole and the protective cover hole together defining a ventilation hole; and
    a ventilation filter disposed between the inner case and the protective cover and extending across both the inner case hole and the protective cover hole, preventing infiltration of liquid into the case;
  wherein air flows in and out of the case through the ventilation hole and a thickness of the case is maintained at a predetermined thickness when outside pressure changes.

2. The radiation image capturing apparatus of claim 1, wherein, the ventilation hole is provided on a side face of the case.

3. The radiation image capturing apparatus of claim 1, wherein,
a protecting cover is attached on a side face of the case so as to cover the side face portion; and
the ventilation filter is provided on an inner side of the protecting cover.

4. The radiation image capturing apparatus of claim 1, wherein, the predetermined thickness is a thickness of a size conforming to JIS Z 4905 in the cassette for screen/film.

5. The radiation image capturing apparatus of claim 1, wherein, the case is a size which is loaded in a bucky apparatus.

6. The radiation image capturing apparatus of claim 1, further comprising:
a cutout portion which is provided in a corner of the case; and
a waterproof cap which is attached to the cutout portion and which seals an opening of the cutout portion to prevent liquid from infiltrating into the case from the cutout portion.

7. The radiation image capturing apparatus of claim 6, wherein, the waterproof cap is formed so that a periphery portion is diagonal with respect to a normal direction of a side face of the case.

8. The radiation image capturing apparatus of claim 2, wherein the ventilation filter is held between the side face portion of the case and the protecting cover.

9. A radiation image capturing apparatus comprising:
a sensor panel which includes a plurality of radiation detecting elements aligned two-dimensionally;
a case which stores the sensor panel;
a ventilation hole which is provided in the case; and
a ventilation filter which is provided in the ventilation hole and which prevents infiltration of liquid into the case,
wherein air flows in and out of the case through the ventilation hole and a thickness of the case is maintained at a predetermined thickness when outside pressure changes;
an inside cover is attached to a side face of the case to seal an opening of the case on a side face portion and a protecting cover is attached so as to cover the inside cover and the side face portion of the case; and
the ventilation filter is provided in a portion of a hole punched in the inside cover;
a hole is punched in the protecting cover and a packing is placed in a portion surrounding the hole provided in the inside cover between the protecting cover and the inside cover; and
the air flows in and out of the case by flowing through the hole provided in the protecting cover and the inside cover, through the ventilation hole formed by a space divided with the protecting cover, the inside cover, and the packing, and through the ventilation filter.

10. The radiation image capturing apparatus of claim 9, wherein a center axis of the hole provided in the protecting cover and a center axis of the hole provided in the inside cover are misaligned.

11. A radiation image capturing apparatus comprising:
a sensor panel which includes a plurality of radiation detecting elements aligned two-dimensionally;
a case which stores the sensor panel;
a ventilation hole which is provided in the case; and
a ventilation filter which is provided in the ventilation hole and which prevents infiltration of liquid into the case,
wherein air flows in and out of the case through the ventilation hole and a thickness of the case is maintained at a predetermined thickness when outside pressure changes;
a side face portion of the case is provided with a first hole;
a protecting cover covering the side face portion of the case is provided with a second hole;
the ventilation hole comprises the first hole and the second hole;
the ventilation filter is positioned between the first hole and the second hole; and
a center axis of the first hole and a second axis of the second hole are misaligned.

* * * * *